(12) United States Patent
Takii et al.

(10) Patent No.: US 11,534,061 B2
(45) Date of Patent: Dec. 27, 2022

(54) SUBJECTIVE OPTOMETRY APPARATUS

(71) Applicant: NIDEK CO., LTD., Aichi (JP)

(72) Inventors: Michihiro Takii, Aichi (JP); Yukito Hirayama, Aichi (JP)

(73) Assignee: NIDEK CO., LTD., Aichi (JP)

( * ) Notice: Subject to any disclaimer, the term of this patent is extended or adjusted under 35 U.S.C. 154(b) by 442 days.

(21) Appl. No.: 16/585,122

(22) Filed: Sep. 27, 2019

(65) Prior Publication Data

US 2020/0100666 A1   Apr. 2, 2020

(30) Foreign Application Priority Data

Sep. 28, 2018 (JP) .............................. JP2018-184057

(51) Int. Cl.
*A61B 3/12* (2006.01)
*A61B 3/02* (2006.01)
*A61B 3/103* (2006.01)
*A61B 3/00* (2006.01)

(52) U.S. Cl.
CPC .............. *A61B 3/0016* (2013.01); *A61B 3/02* (2013.01); *A61B 3/12* (2013.01); *A61B 3/103* (2013.01)

(58) Field of Classification Search
CPC ....... A61B 3/103; A61B 3/028; A61B 3/0016; A61B 3/02; A61B 3/12
USPC .......................................... 351/233, 216, 211
See application file for complete search history.

(56) References Cited

U.S. PATENT DOCUMENTS

| | | | |
|---|---|---|---|
| 9,414,744 B2* | 8/2016 | Kanazawa | A61B 3/18 |
| 9,848,768 B2* | 12/2017 | Kanazawa | A61B 3/032 |
| 2011/0128498 A1 | 6/2011 | Nakamura | |
| 2015/0342455 A1* | 12/2015 | Kanazawa | A61B 3/032 |
| | | | 351/243 |
| 2015/0342459 A1* | 12/2015 | Robert | A61B 3/022 |
| | | | 351/205 |
| 2017/0135572 A1* | 5/2017 | Takii | A61B 3/0041 |

(Continued)

FOREIGN PATENT DOCUMENTS

| | | |
|---|---|---|
| EP | 2 949 266 A1 | 12/2015 |
| JP | 5-024001 U | 3/1993 |

(Continued)

OTHER PUBLICATIONS

Communication dated Apr. 23, 2020, issued by the European Patent Office in counterpart European Application No. 19199748.5.

(Continued)

*Primary Examiner* — Zachary W Wilkes
(74) *Attorney, Agent, or Firm* — Sughrue Mion, PLLC

(57) ABSTRACT

A subjective optometry apparatus includes an optometry unit having an optical member, being located in front of a subject eye, and changing optical characteristics of a target light flus with using the optical member, and a measurement optical system that has a light projecting optical system for applying measurement light emitted from a measurement light source to a fundus of the subject eye through the optometry unit, and a light receiving optical system in which a detector receives reflected light of the measurement light reflected on the fundus of the subject eye through the optometry unit, and that objectively measures the optical characteristics of the subject eye. An optical axis of the measurement optical system is set to be off-axis from an optical axis of the optical member in the optometry unit.

13 Claims, 10 Drawing Sheets

(56) References Cited

U.S. PATENT DOCUMENTS

2018/0064339 A1   3/2018  Takii et al.
2018/0256022 A1   9/2018  Takii et al.
2019/0313904 A1* 10/2019  Dave ........................ A61B 3/10

FOREIGN PATENT DOCUMENTS

| JP | 5-176893 A | | 7/1993 |
| --- | --- | --- | --- |
| JP | 07194540 A | * | 8/1995 |
| JP | 8-182651 A | | 7/1996 |
| JP | 9-108184 A | | 4/1997 |
| JP | 9-253049 A | | 9/1997 |
| JP | 10-155741 A | | 6/1998 |
| JP | 2018-38788 A | | 3/2018 |
| JP | 2018-51224 A | | 4/2018 |

OTHER PUBLICATIONS

Communication dated Aug. 30, 2022 by the Japanese Patent Office in Japanese Patent Application No. 2018-184057.

* cited by examiner

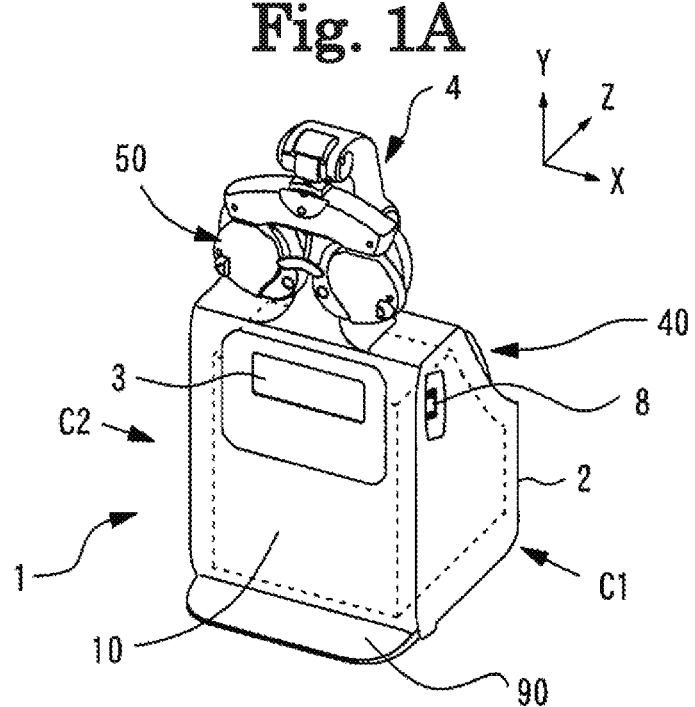
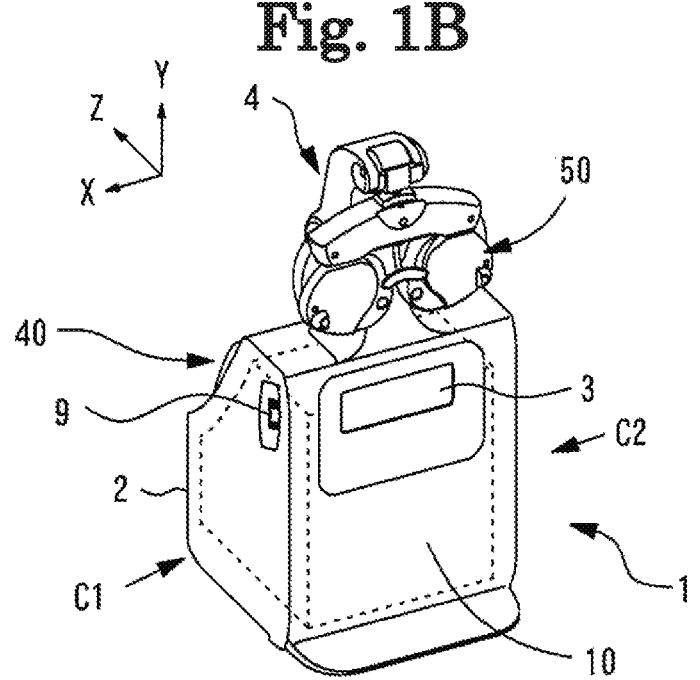

SUBJECTIVE OPTOMETRY APPARATUS

CROSS-REFERENCE TO RELATED APPLICATION

This application claims priority from Japanese Patent Application No. 2018-184057 filed on Sep. 28, 2018, the entire subject-matter of which is incorporated herein by reference.

TECHNICAL FIELD

The present disclosure relates to a subjective optometry apparatus for subjectively measuring optical characteristics of a subject eye.

BACKGROUND

A subjective optometry apparatus is known as follow. An optometry unit to be located in front of a subject eye is used. An optical member such as a spherical lens and a cylindrical (astigmatic) lens is located in an examination window of the optometry unit. Optical characteristics of the subject eye are subjectively examined (measured) by presenting a visual target to the subject eye through the located optical member (refer to JP-A-H05-176893).

Incidentally, in the subjective optometry apparatus configured as described above, a configuration has been reviewed which is equipped with the measurement optical system for objectively measuring the optical characteristics of the subject eye. In this case, the following fact has been understood. If measurement light of the measurement optical system is applied to the subject eye through the optometry unit, the optical characteristics of the subject eye cannot be objectively and satisfactorily measured.

SUMMARY

An object of the present disclosure is to provide a subjective optometry apparatus which can objectively and satisfactorily measure optical characteristics of a subject eye by preventing influence of an optometry unit.

In order to solve the above-described problems, the present disclosure includes the following configurations.

A subjective optometry apparatus for subjectively measuring optical characteristics of a subject eye, including:

an optometry unit configured to have an optical member, be located in front of the subject eye, and change optical characteristics of a target light flux with using the optical member; and a measurement optical system that has a light projecting optical system having a measurement light source which emits measurement light and applying the measurement light emitted from the measurement light source to a fundus of the subject eye through the optometry unit, and a light receiving optical system in which a detector receives reflected light of the measurement light reflected on the fundus of the subject eye through the optometry unit, and that objectively measures the optical characteristics of the subject eye, in which an optical axis of the measurement optical system is set to be off-axis from an optical axis of the optical member in the optometry unit, and the subjective optometry apparatus projects the target light flux on the subject eye through the optometry unit to subjectively measure the optical characteristics of the subject eye.

BRIEF DESCRIPTION OF DRAWINGS

FIGS. 1A and 1B are perspective views illustrating a subjective optometry apparatus when viewed from a front surface side.

DETAILED DESCRIPTION

<Overview>

Figure 2:
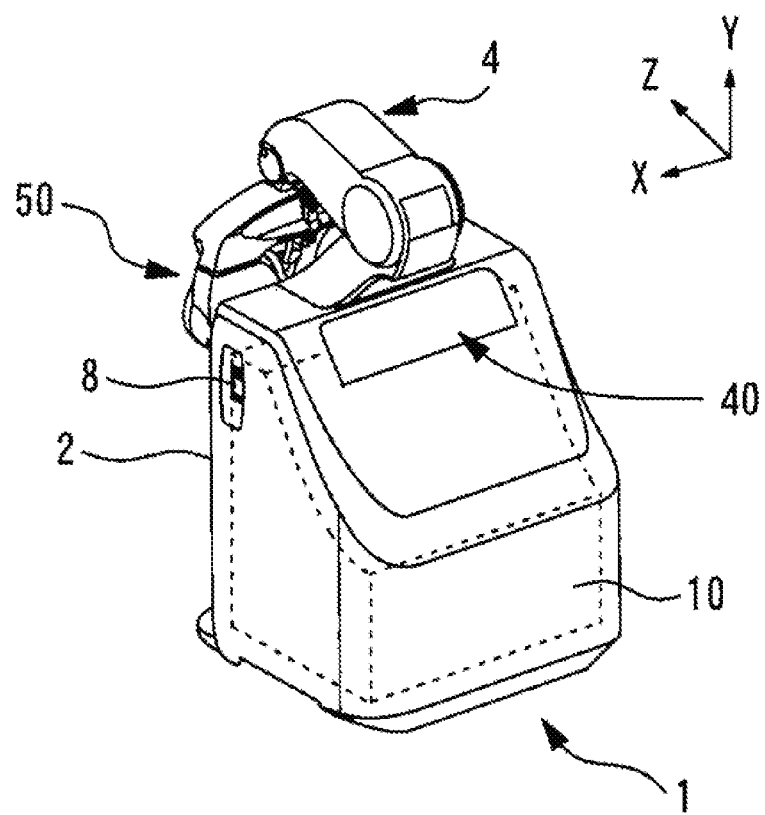
FIG. 2 is a perspective view illustrating the subjective optometry apparatus when viewed from a rear surface side.

Hereinafter, an exemplary embodiment will be described with reference to the drawings. FIGS. 1 to 10 are views for describing a subjective optometry apparatus according to the present embodiment. Items classified using parentheses of < > can be used independently or in association with each other.

In the following description, a depth direction of the subjective optometry apparatus (forward-rearward direction of an examinee when the examinee is measured) will be set as a Z-direction, a horizontal direction on a plane orthogonal to the depth direction (rightward-leftward direction of the examinee when the examinee is measured) will be set as an X-direction, and a vertical direction (upward-downward direction of the examinee when the examinee is measured) will be set as a Y-direction.

For example, the subjective optometry apparatus according to the present embodiment (for example, a subjective optometry apparatus 1) projects a target light flux on the subject eye through an optometry unit (for example, an optometry unit 50), and subjectively measures optical characteristics of the subject eye. For example, the optical characteristics of the subject eye to be subjectively measured subjectively may include at least one of eye refractive power, contrast sensitivity, and a binocular function (for example, a heterophoria amount or a stereoscopic function). For example, as eye refractive power, at least one may be measured between spherical information (for example, spherical power (S)), astigmatism information (for example, at least one of astigmatic power (C) and an astigmatic axis angle (A)).

According to the present embodiment, for example, the subjective optometry apparatus includes the optometry unit. For example, the optometry unit has an optical member (for example, an optical member of a lens disc 57 and a lens 57a), and is located in front of the subject eye so as to change the optical characteristics of the target light flux with using optical member.

For example, the subjective optometry apparatus includes a measurement optical system (for example, a measurement optical system 100) that objectively measures the optical characteristics of the subject eye. For example, the measurement optical system has a light projecting optical system (for example, a light projecting optical system 105) and a light receiving optical system (for example, a light receiving optical system 120). For example, the light projecting optical system has a measurement light source (for example, a measurement light source 130) which outputs measurement light, and applies the measurement light emitted from the measurement light source to a fundus of the examinees eye through the optometry unit. For example, the light projecting optical system may further have an objective optical system (for example, an objective optical system 110). In this case, for example, the objective optical system applies the measurement light emitted from the measurement light source to the fundus of the subject eye through the optometry unit. For example, the light receiving optical system receives reflected light of the measurement light reflected on the fundus of the subject eye with using a detector (for example, a detector 121) through the optometry unit.

For example, according to the present embodiment, in the subjective optometry apparatus, an optical axis (for example, an optical axis L5 or an optical axis L6) of the measurement optical system is set to be off-axis from an optical axis (for example, an optical axis L4) of the optical member in the optometry unit. For example, according to the present embodiment, in the subjective optometry apparatus, the optical axis of the measurement optical system is set to be off-axis from the optical axis of the optical member in the optometry unit so as to prevent the light receiving optical system from detecting the reflected light generated by the measurement light reflected on the optical member of the optometry unit.

In this way, for example, the subjective optometry apparatus has the measurement light source that outputs the measurement light, the light projecting optical system that applies the measurement light emitted from the measurement light source to the fundus of the subject eye through the optometry unit, and the light receiving optical system that receives the reflected light of the measurement light reflected on the fundus of the subject eye with using the detector through the optometry unit, and includes the measurement optical system that objectively measures the optical characteristics of the subject eye. The optical axis of the measurement optical system is set to be off-axis from the optical axis of the optical member in the optometry unit. In this manner, it is possible to prevent a possibility that the optical characteristics of the subject eye cannot be satisfactorily measured since the measurement light of the light projecting optical system in the measurement optical system is reflected on the optical member of the optometry unit, which causes the reflected light from the optical member of the optometry unit to be detected together with the reflected light reflected on the subject eye. That is, the reflected light from the optical member of the optometry unit is prevented from being detected by the detector. In this manner, it is possible to prevent a possibility that the optical characteristics of the subject eye cannot be satisfactorily measured.

For example, as a configuration in which the optical axis of the measurement optical system is set to be off-axis from the optical axis of the optical member in the optometry unit, a configuration may be adopted in which at least one of the optical axis of the light projecting optical system and the optical axis of the light receiving optical system is set to be off-axis. In this case, for example, at least one of the optical axis (for example, the optical axis L5) of the light projecting optical system in the measurement optical system and the optical axis (for example, the optical axis L6) of the light receiving optical system is set to be off-axis from the optical axis (for example, the optical axis L6) of the optical member in the optometry unit. In this manner, the optical axis of the measurement optical system may be set to be off-axis from the optical axis of the optical member in the optometry unit. For example, according to the present embodiment, in the subjective optometry apparatus, at least one of the optical axis of the light projecting optical system in the measurement optical system and the optical axis of the light receiving optical system is set to be off-axis from the optical axis of the optical member in the optometry unit so that the reflected light generated by the measurement light from the light projecting optical system being reflected on the optical member of the optometry unit is not detected by the light receiving optical system.

For example, the light projecting optical system may adopt a configuration as follows. In a case where the optical axis of the light projecting optical system is set to be coaxial with the optical axis of the optical member in the optometry unit, the optical axis of the light receiving optical system may be set to be off-axis from the optical axis of the optical member in the optometry unit.

For example, in a case where the light receiving optical system is set so that the optical axis of the light receiving optical system is coaxial with the optical axis of the optical member in the optometry unit, a configuration may be adopted in which the optical axis of the light receiving optical system is off-axis from the optical axis of the optical member in the optometry unit. As the light receiving optical system, it is preferable that the light receiving optical system is located at a position where the reflected light of the measurement light of the measurement optical system is less likely to be detected by the optical member in the optometry unit. For example, a configuration may be adopted in which at least some optical members of the objective optical system in the light projecting optical system and the light receiving optical system may be shared in use. As a matter of course, both of these may be respectively configured to include a separate optical member.

For example, in a configuration in which the optical axis of the light projecting optical system is set to be off-axis from the optical axis of the optical member in the optometry unit, the measurement light source is set to be off-axis in the configuration. In this manner, the optical axis of the light projecting optical system may be set to be off-axis. In this case, for example, the optical axis of the measurement light source is set to off-axis from the optical axis of the optical member in the optometry unit. In this manner, the optical axis of the light projecting optical system may be set to be off-axis from the optical axis of the optical member in the optometry unit.

For example, in a configuration in which the optical axis of the light projecting optical system is set to be off-axis from the optical axis of the optical member in the optometry unit, the objective optical system of the light projecting optical system is set to be off-axis in the configuration. In this manner, the optical axis of the light projecting optical system may be set to be off-axis. In this case, for example, the optical axis of the objective optical system is set to off-axis from the optical axis of the optical member in the optometry unit. In this manner, the optical axis of the light projecting optical system may be set to be off-axis from the optical axis of the optical member in the optometry unit.

For example, the subjective optometry apparatus may further include a projection optical system (for example, a projection optical system 10) and a housing (for example, a housing 2). For example, the projection optical system may have a visual target presenting portion that emits a target light flux, and may project the target light flux emitted from the visual target presenting portion toward the subject eye. For example, the housing may house the projection optical system. In this case, for example, the optometry unit may be located outside the housing, and may change the optical characteristics of the target light flux emitted from the visual target presenting portion with using the optical member.

For example, as a position for locating the light projecting optical system, the light projecting optical system can be located at any desired position. In addition, for example, as a position for locating the light receiving optical system, the light receiving optical system can be located at any desired position.

For example, in a case where the subjective optometry apparatus includes the projection optical system and the housing, the light projecting optical system may be located inside the housing. In this case, for example, the light projecting optical system may be located inside the housing. As an example, a configuration may be adopted as follows. The measurement light from the light projecting optical system is emitted from the inside of the housing through at least some members of the projection optical system, and the measurement light is output to the optometry unit outside the housing. In addition, as an example, a configuration may be adopted in which the measurement light is output from the inside of the housing to the optometry unit outside the housing without passing through a member of the projection optical system. In this case, for example, the light receiving optical system may be located either inside or outside the housing.

In addition, for example, in a case where the subjective optometry apparatus includes the projection optical system and the housing, the light projecting optical system may be located outside the housing. In this case, for example, the light projecting optical system may be located between the optometry unit and the housing. As an example, the light projecting optical system may be located in the optometry unit. That is, the light projecting optical system may be located integrally with the optometry unit. In this case, for example, the light receiving optical system may be located either inside or outside the housing.

For example, in a case where the subjective optometry apparatus includes the projection optical system and the housing, at least some members of the light projecting optical system may be located outside the housing. As an example, in a case where the light projecting optical system has the measurement light source and the objective optical system, at least some members of the measurement light source and the objective optical system may be located outside the housing. In addition, for example, at least some members of the light receiving optical system may be located outside the housing.

For example, in a configuration in which the optical axis of the measurement optical system is set to be off-axis from the optical axis of the optical member in the optometry unit, a configuration may be adopted in which one optical axis between the optical axis of the measurement optical system and the optical axis of the optical member in the optometry unit is coaxial with a visual axis (for example, the optical axis L4) set for the subject eye to view the target light flux which is projected in a frontal direction. In the present embodiment, the terms of coaxial includes substantially coaxial. In this case, for example, the optical axis of the measurement optical system may be coaxial with the visual axis set for the subject eye to view the target light flux which is projected in the frontal direction. The optical axis of the optical member in the optometry unit may be located so that the optical axis of the optical member in the optometry unit is off-axis from the optical axis of the measurement optical system. That is, the optical member of the optometry unit may be set so that the optical axis of the optical member of the optometry unit is off-axis from the visual axis.

In addition, for example, the optical axis of the optical member in the optometry unit may be coaxial with the visual axis set for the subject eye to view the target light flux which is projected in the frontal direction. The measurement optical system may be set so that the optical axis of the measurement optical system is off-axis from the optical axis of the optical member in the optometry unit. That is, the measurement optical system may be set so that the optical axis of the measurement optical system is off-axis from the visual axis. In this way, for example, the optical axis of the optical member in the optometry unit may be coaxial with the visual axis set for the subject eye to view the target light flux which is projected in the frontal direction. The measurement optical system may be located so that the optical axis of the measurement optical system is off-axis from the optical axis of the optical member in the optometry unit. In this manner, compared to a configuration in which the visual axis and the optical axis of the measurement optical system are coaxial with each other and the optical member of the optometry unit is located so that the optical axis of the optical member of the optometry unit is set to be off-axis from the optical axis of the measurement optical system, an easier configuration can prevent a possibility that the reflected light from the optical member of the optometry unit may be detected by the detector.

For example, in a configuration in which one optical axis between the optical axis of the measurement optical system and the optical axis of the optical member in the optometry unit, and the optical axis of one of the optical axis is coaxial with the visual axis set for the subject eye to view the target light flux which is projected in the frontal direction, the above-described configuration may be applied to at least one of the light projecting optical system serving as the measurement optical system and the light receiving optical system.

For example, in a case where the above-described configuration is applied to the light projecting optical system, in a configuration in which the optical axis of the light projecting optical system is set to be off-axis from the optical axis of the optical member in the optometry unit, a configuration may be adopted as follows. One optical axis between the optical axis of the light projecting optical system and the optical axis of the optical member in the optometry unit is coaxial with the visual axis (for example, the optical axis L4) set for the subject eye to view the target light flux which is projected in the frontal direction. In the present embodiment, the term of coaxial includes substantially coaxial. In this case, for example, the optical axis of the light projecting optical system may be coaxial with the visual axis set for the subject eye to view the target light flux which is projected in the frontal direction. The optical member in the optometry unit may be located so that the optical axis of the optical member in the optometry unit is off-axis from the optical axis of the light projecting optical system. That is, the optical member of the optometry unit may be set so that the optical axis of the optical member of the optometry unit is off-axis from the visual axis.

In addition, in this case, for example, the optical axis of the optical member in the optometry unit may be coaxial with the visual axis set for the subject eye to view the target light flux which is projected in the frontal direction. The light projecting optical system may be set so that the optical axis of the light projecting optical system is off-axis from the optical axis of the optical member in the optometry unit. That is, the light projecting optical system may be set so that the optical axis of the light projecting optical system is off-axis from the visual axis. In this way, for example, the optical axis of the optical member in the optometry unit may be coaxial with the visual axis set for the subject eye to view the target light flux which is projected in the frontal direction. The light projecting optical system may be located so that the optical axis of the light projecting optical system is off-axis from the optical axis of the optical member in the optometry unit. In this manner, compared to a case where the visual axis and the optical axis of the light projecting optical system are coaxial with each other and the optical member of the optometry unit is located so that the optical axis of the optical member of the optometry unit is set to be off-axis from the optical axis of the light projecting optical system, an easier configuration can prevent a possibility that the reflected light from the optical member of the optometry unit may be detected by the detector.

As a matter of course, in a configuration in which the optical axis of the light projecting optical system is off-axis from the optical axis of the optical member in the optometry unit, a configuration may be adopted as follows. Both the optical axes of the optical axis of the light projecting optical system and the optical axis of the optical member in the optometry unit are off-axis from the visual axis set for the subject eye to view the target light flux which is projected in the frontal direction.

For example, in a case where the above-described configuration is applied to the light receiving optical system, in a configuration in which the optical axis of the light receiving optical system is set to be off-axis from the optical axis of the optical member in the optometry unit, a configuration may be adopted as follows. One optical axis between the optical axis of the light receiving optical system and the optical axis of the optical member in the optometry unit are coaxial with the visual axis (for example, the optical axis L4) set for the subject eye to view the target light flux which is projected in the frontal direction. In the present embodiment, the term of coaxial includes substantially coaxial. In this case, for example, the optical axis of the light receiving optical system may be coaxial with the visual axis set for the subject eye to view the target light flux which is projected in the frontal direction. The optical member in the optometry unit may be located so that the optical axis of the optical member in the optometry unit is off-axis from the optical axis of the light receiving optical system. That is, the optical member of the optometry unit may be set so that the optical axis of the optical member of the optometry unit is off-axis from the visual axis.

In addition, in this case, for example, the optical axis of the optical member in the optometry unit may be coaxial with the visual axis set for the subject eye to view the target light flux which is projected in the frontal direction. The light receiving optical system may be set so that the optical axis of the light receiving optical system is off-axis from the optical axis of the optical member in the optometry unit. That is, the light receiving optical system may be set so that the optical axis of the light receiving optical system is off-axis from the visual axis. In this way, for example, the optical axis of the optical member in the optometry unit may be coaxial with the visual axis set for the subject eye to view the target light flux which is projected in the frontal direction. The light receiving optical system may be located so that the optical axis of the light receiving optical system is off-axis from the optical axis of the optical member in the optometry unit. In this manner, compared to a configuration in which the visual axis and the optical axis of the light receiving optical system are coaxial with each other and the optical member of the optometry unit is located so that the optical axis of the optical member of the optometry unit is set to be off-axis from the optical axis of the light receiving optical system, an easier configuration can prevent a possibility that the reflected light from the optical member of the optometry unit from may be detected by the detector.

As a matter of course, in a configuration in which the optical axis of the light receiving optical system is off-axis from the optical axis of the optical member in the optometry unit, a configuration may be adopted as follows. Both the optical axes of the optical axis of the light receiving optical system and the optical axis of the optical member in the optometry unit are off-axis from the visual axis set for the subject eye to view the target light flux which is projected in the frontal direction.

For example, in a case where the above-described configuration is applied to the light projecting optical system and the light receiving optical system, in a configuration in which the optical axis of the light projecting optical system is set to be off-axis from the optical axis of the optical member in the optometry unit, a configuration may be adopted as follows. One optical axis between the optical axis of the light projecting optical system and the light receiving optical system and the optical axis of the optical member in the optometry unit is coaxial with the visual axis (for example, the optical axis L4) set for the subject eye to view the target light flux which is projected in the frontal direction. In the present embodiment, the term of coaxial includes substantially coaxial. In this case, for example, the optical axis of the light projecting optical system and the optical axis of the light receiving optical system may be coaxial with the visual axis set for the subject eye to view the target light flux which is projected in the frontal direction. The optical member in the optometry unit may be located so that the optical axis of the optical member in the optometry unit is off-axis from the optical axis of the light projecting optical system and the optical axis of the light receiving optical system. That is, the optical member of the optometry unit may be set so that the optical axis of the optical member of the optometry unit is off-axis from the visual axis.

In addition, in this case, for example, the optical axis of the optical member in the optometry unit may be coaxial with the visual axis set for the subject eye to view the target light flux which is projected in the frontal direction. The light projecting optical system and the light receiving optical system may be set so that the optical axis of the light projecting optical system and the optical axis of the light receiving optical system is off-axis from the optical axis of the optical member in the optometry unit. That is, the light projecting optical system and the light receiving optical system may be set so that the optical axis of the light projecting optical system and the optical axis of the light receiving optical system are off-axis from the visual axis. In the above-described case, the optical axis of the light projecting optical system and the optical axis of the light receiving optical system may be coaxial with each other, or may be axes different from each other. In this way, for example, the optical axis of the optical member in the optometry unit may be coaxial with the visual axis set for the subject eye to view the target light flux which is projected in the frontal direction. The light projecting optical system and the light receiving optical system may be located so that the optical axis of the light projecting optical system and the optical axis of the light receiving optical system are off-axis from the optical axis of the optical member in the optometry unit. In this manner, compared to a configuration in which the visual axis, the optical axis of the light receiving optical system, and the light receiving optical system are coaxial with each other and the optical member of the optometry unit is located so that the optical axis of the optical member of the optometry unit is off-axis from the optical axis of the light projecting optical system and the light receiving optical system, an easier configuration can prevent a possibility that the reflected light from the optical member of the optometry unit may be detected by the detector.

As a matter of course, in a configuration in which the optical axis of the light projecting optical system and the optical axis of the light receiving optical system are off-axis from the optical axis of the optical member in the optometry unit, a configuration may be adopted as follows. All of the optical axes including the optical axis of the light projecting optical system, the optical axis of the light receiving optical system, the optical axis of the optical member in the optometry unit are off-axis from the visual axis set for the subject eye to view the target light flux which is projected in the frontal direction.

<Off-Axis Configuration>

Hereinafter, a configuration for setting the light projecting optical system to be off-axis will be described as an example. As a matter of course, the light receiving optical system can also be set to be off-axis with using a configuration which is the same as that of the light projecting optical system. In the following description, description of an off-axis configuration of the light receiving optical system will be omitted since the light projecting optical system can be similarly described.

For example, in the present embodiment, the subjective optometry apparatus is set so that the optical axis of the light projecting optical system is off-axis from the optical axis of the optical member in the optometry unit. For example, as the off-axis configuration, the optical axis of the light projecting optical system is inclined from the optical axis of the optical member in the optometry unit. In this manner, the subjective optometry apparatus may be set so that the optical axis of the light projecting optical system is off-set from the optical axis of the optical member in the optical unit. In this case, for example, the subjective optometry apparatus may be located in such a way that at least one optical axis between the optical axis of the light projecting optical system and the optical axis of the optical member in the optometry unit is inclined from the other optical axis. That is, for example, the subjective optometry apparatus is located so that at least one of the optical axis of the light projecting optical system and the optical axis of the optical member in the optometry unit is inclined. In this manner, a configuration may be adopted in which the optical axis of the light projecting optical system and the optical axis of the optical member in the optometry unit are not coaxial with each other.

For example, in a configuration in which at least one optical axes is located to be inclined from the other optical axis, the subjective optometry apparatus may be located in such a way that at least one optical axis of the optical axis of the measurement light source in the light projecting optical system and the optical axis of the optical member in the optometry unit is inclined from the other optical axis. For example, in a configuration in which at least one optical axis is located to be inclined from the other optical axis, in a case where the light projecting optical system has the measurement light source and the objective optical system, the subjective optometry apparatus may be located so that at least one optical axis of the optical axis of the objective optical system and the optical axis of the optical member in the optometry unit is inclined from the other optical axis.

For example, as a configuration in which the optical axis of the light projecting optical system is inclined from the optical axis of the optical member in the optometry unit, a configuration may be adopted as follows. The optical axis of at least some optical members of the light projecting optical system is inclined. For example, in a case where the light projecting optical system has the measurement light source and the objective optical system, the subjective optometry apparatus may be located in such a way that at least one of the measurement light source and the objective optical system is inclined from the optical axis of the optical member in the optometry unit.

For example, as a configuration in which the optical axis of the optical member in the optometry unit is inclined from the optical axis of the light projecting optical system, a configuration may be adopted as follows. The optical axis of at least some optical members of the optical members in the optical unit is inclined. For example, in a case where as the optical members of the optometry unit include a protective cover (for example, a protective cover 65) and the optical members (for example, the optical member of the lens disc 57 and the lens 57a) different from the protective cover, the subjective optometry apparatus may be located in such a way that only the protective cover is inclined from the optical axis of the light projecting optical system. Alternatively, both the protective cover and the optical member different from the protective cover are inclined from the optical axis of the projecting optical system.

For example, a configuration in which the optical axis of the light projecting optical system is inclined from the optical axis of the optical member in the optometry unit represents a configuration in which an angle (inclination angle) formed between the optical axis of the light projecting optical system and the optical axis of the optical member in the optometry unit is not 0°. For example, the inclination angle may be 5° to 20°. As a matter of course, without being limited thereto, the inclination angle can be set to any desired angle (for example, 1° or 25°).

For example, in a configuration in which the optical axis of the light projecting optical system is inclined from the optical axis of the optical member in the optometry unit, a configuration may be adopted as follows. One optical axis of the optical axis of the light projecting optical system and the optical axis of the optical member in the optometry unit is coaxial with the visual axis set for the subject eye to view the target light flux which is projected in the frontal direction. In the above-described configuration, the term of coaxial includes substantially coaxial.

In this case, for example, the optical axis of the light projecting optical system may be coaxial with the visual axis set for the subject eye to view the target light flux which is projected in the frontal direction. The optical axis of the optical member in the optometry unit may be inclined from the optical axis of the objective lens. That is, the subjective optometry apparatus may be located in such a way that the optical axis of the optical member of the optometry unit is inclined from the visual axis.

In addition, in this case, for example, the optical axis of the optical member in the optometry unit may be coaxial with the visual axis set for the subject eye to view the target light flux which is projected in the frontal direction. The subjective optometry apparatus may be located in such a way that the optical axis of the objective optical system is inclined from the optical axis of the optical member in the optometry unit. That is, the subjective optometry apparatus may be located in such a way that the optical axis of the objective optical system is inclined from the visual axis. In this manner, compared to a configuration in which the optical member of the optometry unit is inclined from the visual axis, an easier configuration can prevent a possibility that the reflected light from the optical member of the optometry unit may be detected by the detector.

As described above, in a case of the configuration in which the optical axis of the light projecting optical system is inclined from the visual axis, the subjective optometry apparatus may be located so that the optical axis of some optical members of the optical members of the optical unit is further inclined from the visual axis. For example, the subjective optometry apparatus may be located so that at least the protective cover in the optical members in the optometry unit is inclined. In this case, for example, a configuration may be adopted as follows. The optical members include the protective cover and the optical member different from the protective cover, and the optical axis of at least the protective cover is inclined from the visual axis. In this way, in the optical members of the optometry unit, the protective cover serving as the optical member which is not driven is inclined. In this manner, it is possible to further prevent a possibility that the reflected light from the optometry unit may be detected by the detector. That is, the protective cover serving as the optical member which is not driven in the optical members of the optometry unit is inclined.

For example, in a configuration in which the optical axis of the light projecting optical system is inclined from the optical axis of the optical member in the optometry unit, a configuration may be adopted as follows. The subjective optometry apparatus is located in such a way that both the optical axes including the optical axis of the light projecting optical system and the optical axis of the optical member in the optometry unit are inclined from the visual axis set for the subject eye to view the target light flux which is projected in the frontal direction.

For example, as the off-axis configuration, the optical axis of the light projecting optical system is eccentric from the optical axis of the optometry unit. In this manner, the optical axis of the light projecting optical system may be set to be off-axis from the optical axis of the optometry unit. In this case, for example, the subjective optometry apparatus may be located in such a way that at least one optical axis of the optical axis of the light projecting optical system and the optical axis of the optical member in the optometry unit is eccentric from the other optical axis. That is, for example, the subjective optometry apparatus is located in such a way that at least one of the optical axis of the light projecting optical system and the optical axis of the optical member of the optometry unit is eccentric. In this manner, the optical axis of the light projecting optical system and the optical axis of the optical member in the optometry unit may not be coaxial with each other.

For example, in a configuration in which at least one optical axes is located to be eccentric from the other optical axis, the subjective optometry apparatus may be located in such a way that at least one optical axis of the optical axis of the measurement light source in the light projecting optical system and the optical axis of the optical member in the optometry unit is eccentric from the other optical axis. For example, in a configuration in which at least one optical axis is located to be inclined from the other optical axis, in a case where the light projecting optical system has the measurement light source and the objective optical system, the subjective optometry apparatus may be located in such a way that at least one optical axis of the optical axis of the objective optical system and the optical axis of the optical member in the optometry unit is eccentric from the other optical axis.

For example, as a configuration in which the optical axis of the light projecting optical system is eccentric from the optical axis of the optical member in the optometry unit, a configuration may be adopted as follows. The optical axis of at least some of the optical members of the light projecting optical system is eccentric. For example, in a case where the light projecting optical system has the measurement light source and the objective optical system, the subjective optometry apparatus may be located in such a way that at least one of the measurement light source and the objective optical system is eccentric from the optical axis of the optical member in the optometry unit.

For example, as a configuration in which the optical axis of the optical member in the optometry unit is eccentric from the optical axis of the light projecting optical system, a configuration may be adopted as follows. The optical axis of at least some optical members out of the optical members in the optical unit is eccentric. For example, in a case where there are a plurality of the optical members of the optometry unit, at least some optical members out of the plurality of optical members may be eccentric.

For example, a configuration in which the optical axis of the light projecting optical system is eccentric from the optical axis of the optical member in the optometry unit represents a configuration in which the optical axis of the light projecting optical system is shifted in a state of being orthogonal to an orthogonal plane on the orthogonal plane orthogonal to the optical axis of the optical member in the optometry unit. For example, the optical axis of the light projecting optical system is eccentric from the optical axis of the optical member in the optometry unit. In this manner an incident angle is changed when the measurement light emitted from the objective optical system is incident on the optical member in the optometry unit. For example, the amount of the above-described shift (shift amount) may be 1 mm to 10 mm. As a matter of course, without being limited thereto, the shift amount (movement amount) can be set to any desired shift amount (for example, 0.5 mm or 15 mm).

For example, in a configuration in which the optical axis of the light projecting optical system is eccentric with the optical axis of the optical member in the optometry unit, a configuration may be adopted as follows. One optical axis of the optical axis of the light projecting optical system and the optical axis of the optical member in the optometry unit is coaxial with the visual axis set for the examinee's eye to view the target light flux which is projected in the frontal direction. In the above-described configuration, the term of coaxial includes substantially coaxial.

In this case, for example, the optical axis of the light projecting optical system may be coaxial with the visual axis set for the subject eye to view the target light flux which is projected in the frontal direction. The subjective optometry apparatus may be located in such a way that the optical axis of the optical member in the optometry unit is eccentric from the optical axis of the light projecting optical system. That is, the subjective optometry apparatus may be located in such a way that the optical axis of the optical member of the optometry unit is eccentric from the visual axis.

In addition, in this case, for example, the optical axis of the optical member in the optometry unit may be coaxial with the visual axis set for the subject eye to view the target light flux which is projected in the frontal direction. The optical axis of the light projecting optical system may be located to be eccentric from the optical axis of the optical member in the optometry unit. That is, the optical axis of the light projecting optical system may be located to be eccentric from the visual axis. In this manner, compared to a configuration in which the optical member of the optometry unit is located to be eccentric from the visual axis, an easier configuration can prevent the reflected light from the optical member of the optometry unit from being detected by the detector.

For example, in a configuration in which the optical axis of the light projecting optical system is eccentric from the optical axis of the optical member in the optometry unit, a configuration may be adopted as follows. Both the optical axes including the optical axis of the light projecting optical system and the optical axis of the optical member in the optometry unit are located to be eccentric from the visual axis set for the subject eye to view the target light flux which is projected in the frontal direction.

For example, a plurality of configurations for setting the optical axis of the light projecting optical system to be off-axis from the optical axis of the optical member in the optometry unit may be combined with each other. For example, the present disclosure may adopt both configurations including a configuration in which the optical axis of the light projecting optical system is eccentric from the optical axis of the optical member in the optometry unit and a configuration in which the optical axis of the light projecting optical system is inclined from the optical axis of the optical member in the optometry unit.

The configuration described above in <the off-axis configuration> can also be applied to the light receiving optical system. For example, in a configuration in which the light receiving optical system is set to be off-axis, the optical axis of the light receiving optical system is inclined from the optical axis of the optical member in the optometry unit. In this manner, the optical axis of the light receiving optical system may be set to be off-axis from the optical axis of the optical member in the optometry unit. In addition, for example, in a configuration in which the light receiving optical system is set to be off-axis, the optical axis of the light receiving optical system is eccentric from the optical axis of the optical member in the optometry unit. In this manner, the optical axis of the light receiving optical system may be set to be off-axis from the optical axis of the optical member in the optometry unit.

Hereinafter, each configuration of the subjective optometry apparatus according to the present embodiment will be described in more detail.

<Optometry Unit>

For example, the optometry unit may be configured to change the optical characteristics of the target light flux (for example, spherical power, cylindrical power (astigmatic power), an astigmatic axis angle, polarization characteristics, and an aberration amount). For example, as a configuration for changing the optical characteristics of the target light flux, a configuration for controlling the optical member may be adopted. For example, as the optical member, at least one of a spherical lens, a cylinder lens, a cross cylinder lens, a rotary prism, a wavefront modulation element, and a variable focal length lens may be used. As a matter of course, for example, as the optical member, another optical member different from the above-described optical member may be used. For example, as the optical member, the protective cover may be used. For example, the protective cover is located in an examination window (for example, an examination window 53) in order to protect the optical member different from the protective cover.

For example, as the optometry unit, another optometry unit (phoropter) may be used in which the optical members arranged in front of the subject eye are switched and arranged. For example, the optometry unit may be configured to include a pair of right and left lens chamber units for switching and arranging the optical members in the examination window. For example, the optometry unit may have a lens disc in which a plurality of optical members are arranged on the same circumference, and a driving unit for rotating the lens disc. The optometry unit may be configured to electrically switch the optical members by driving the driving unit (for example, a motor).

<Measurement Optical System>

For example, the measurement optical system may be an optical system which measures eye refractive power of the subject eye as the optical characteristics. As a matter of course, for example, the measurement optical system may be an optical system which measures the optical characteristics different from the eye refractive power. For example, as the measurement optical system for measuring the eye refractive power, a configuration may be adopted as follows. Spot-like measurement light is applied to a fundus, and reflected light thereon is extracted in a ring shape so as to detect the ring-shaped fundus reflected light. In this case, for example, the measurement light source may output the measurement light, and the objective optical system may apply the spot-like measurement light to the fundus of the subject eye through the optical member of the optometry unit and a pupil center portion of the subject eye. In addition, for example, the light receiving optical system may extract the fundus reflected light reflected from the fundus into a ring shape through a pupil peripheral portion and the optical member of the optometry unit, and may cause the detector to detect the ring-shaped fundus reflected light.

In addition, as the measurement optical system for measuring the eye refractive power, a configuration may be adopted as follows. The ring-shaped measurement light is projected on the fundus from the pupil peripheral portion, and the fundus reflected light is extracted from the pupil center portion so that the detector detects a ring-shaped fundus reflection image. In this case, for example, the measurement light source may output the measurement light, and the objective optical system may apply the ring-shaped measurement light to the fundus of the subject eye through the optical member of the optometry unit and the pupil peripheral portion of the subject eye. In addition, for example, the light receiving optical system may extract the fundus reflected light reflected from the fundus into the ring shape through the pupil center portion and the optical member of the optometry unit, and may cause the detector to detect the ring-shaped fundus reflected light.

In addition, for example, as the measurement optical system for measuring the eye refractive power, a configuration may be adopted in which the measurement is performed using a photo-fraction method. In this case, for example, as the measurement optical system, a configuration may be adopted as follows. The measurement light is applied to the subject eye fundus, and is reflected on the subject eye fundus so as to detect reflection distribution of a pupil portion from the fundus reflected light through the pupil portion.

For example, the measurement optical system for measuring the eye refractive power is not limited to the above-described configuration. For example, as the measurement optical system, a configuration may be adopted as follows. The measurement light is applied to the subject eye so as to detect the reflected light. In this manner, the optical characteristics can be objectively measured. For example, the measurement optical system may be configured to include a Shack-Hartmann sensor. In addition, for example, the measurement optical system may be configured to have a phase difference method of projecting a slit on the subject eye.

<Projection Optical System>

For example, as a visual target presenting portion, a display may be used. For example, the display may be at least one of a liquid crystal display (LCD), a liquid crystal on silicon (LCOS), an organic electro luminescence (EL). For example, the display displays an examination visual target such as a Landolt ring visual target.

In addition, for example, as the visual target presenting portion, a digital micromirror device (DMD) may be used. In general, the DMD has high reflectance, and is bright. Therefore, even in a case of using polarized light, the amount of light of the target light flux can be maintained, compared to the liquid crystal display.

In addition, for example, the visual target presenting portion may be configured to have a visual target presenting visible light source and a visual target plate. In this case, for example, the visual target plate is a rotatable disc plate and has a plurality of visual targets. For example, the plurality of targets include visual acuity test visual targets used for subjective measurement. For example, as the visual acuity test visual target, visual targets are prepared for each visual acuity value (visual acuity values 0.1, 0.3, . . . , 1.5). For example, the visual target plate is rotated by a motor, and the visual targets are switched and arranged on an optical path through which the target light flux is guided to the subject eye. As a matter of course, as the visual target presenting portion for projecting the target light flux, the visual target presenting portion having a configuration other than the above-described configuration may be used.

For example, the projection optical system may have at least one or more optical members for projecting the target light flux on the subject eye. For example, the projection optical system may have a projection optical member for guiding an image of the target light flux emitted from the visual target presenting portion to the subject eye so as to optically obtain a predetermined examination distance (for example, a concave mirror 13).

For example, the projection optical system projects the target light flux on the subject eye by causing the target light flux emitted from the visual target presenting portion to be incident thereon so as to be shifted from the optical axis of the optical member. In this case, for example, the visual target presenting portion may be located by causing a normal direction with respect to a screen of the visual target presenting portion to be inclined from the optical axis of the projection optical member.

For example, the projection optical member may be at least one of the concave mirror and the lens. For example, in a case where the projection optical member is the concave mirror, the projection optical system may have a reflection member (for example, a flat mirror 12) which causes the target light flux emitted from the visual target presenting portion to be reflected on the concave mirror so as to guide the target light flux from the inside to the outside of the housing. According to this configuration, the number of members in the projection optical system can be reduced, and a space for the subjective optometry apparatus can be further reduced. As a matter of course, the projection optical system is not limited to the above-described configuration. Any configuration may be adopted as long as the target light flux is projected on the subject eye by causing the target light flux emitted from the visual target presenting portion to be incident thereon so as to be shifted from the optical axis of the optical member.

For example, as the reflection member, any one of a mirror (for example, a total reflection mirror or a half mirror) and a prism may be used. As a matter of course, without being limited thereto, the reflection member may be any member which guides the target light flux to the subject eye.

For example, in the present embodiment, the projection optical system may have a right eye projection optical system and a left eye projection optical system disposed in pair on the right and left sides. In this case, for example, a pair of right and left visual target presenting portions may be used. For example, in the right eye projection optical system and the left eye projection optical system, members configuring the right eye projection optical system and members configuring the left eye projection optical system may be configured to include the same member. In addition, for example, in the right eye projection optical system and the left eye projection optical system, at least some members of the members configuring the right eye projection optical system and the members configuring the left eye projection optical system may be configured to include a different member. For example, in the right eye projection optical system and the left eye projection optical system, at least some members of the members configuring the right eye projection optical system and the members configuring the left eye projection optical system may be configured to be shared in use. In addition, for example, in the right eye projection optical system and the left eye projection optical system for the left eye, the members configuring the right eye projection optical system and the members configuring the left eye projection optical system may be configured to be provided separate from each other.

<Holding Unit>

For example, the subjective optometry apparatus may include a holding unit (for example, a holding arm 35) which holds the optometry unit. For example, in the subjective optometry apparatus, the housing and the optometry unit may be integrally linked to each other. As an example, for example, in the holding unit, the housing and the optometry unit may be integrally linked to each other.

For example, the subjective optometry apparatus may have a configuration in which the examination window of the optometry unit and a presentation window (for example, a presentation window 3) of the housing are arranged to face each other.

For example, instead of a configuration in which the housing and the optometry unit are constantly linked to each other, the subjective optometry apparatus may be configured so that both of these are close to each other. For example, as the configuration in which both of these are arranged close to each other, a distance may exist between the optometry unit and the housing so that an examiner's head cannot enter. For example, as the configuration in which both of these are arranged close to each other, a distance between the optometry unit and the housing may be 1 m or shorter (for example, 1 m, 500 mm, 135 mm, or 70 mm). As a matter of course, for example, as the configuration in which both of these are arranged close to each other, a configuration may be adopted in which the distance between the optometry unit and the housing is longer than 1 m.

<Correction Unit>

For example, in the present embodiment, the measurement result of the measurement optical system which is measured through the optical member of the optometry unit may be corrected. For example, the subjective optometry apparatus may include a correction unit which corrects the optical characteristics of the subject eye measured by the measurement optical system, based on a change amount of the optical characteristics of the target light flux detected by the optical member. In this manner, for example, in a case where the measurement light is applied to the subject eye through the optometry unit so as to obtain the measurement result, even if the optical characteristics of the measurement result is changed in accordance with the optical member set in the optometry unit, the measurement result can be acquired in view of the change. That is, satisfactory measurement results can be acquired regardless of the optical member set in the optometry unit.

For example, in a case where predetermined spherical power is corrected in the optometry unit, a value of the spherical power in the objective measurement result may be corrected through differential processing performed on a value of the spherical power in the objectively measured result and a value of the spherical power changed by the optical member of the optometry unit. In the above-described configuration, although the spherical power is described as an example, the present embodiment is not limited thereto. For example, the astigmatic power or the astigmatic axis angle may be corrected. As a matter of course, the optical characteristics (for example, a prism) different from the above-described optical characteristics may be corrected.

For example, a configuration may be adopted as follows. Information on the change amount of the optical characteristics of the target light flux detected by the optometry unit is acquired by the examiner who operates an operation unit (for example, a controller 81) so that the correction unit receives the information on the change amount of the optical characteristics of the target light flux which is input to the subjective optometry apparatus. In addition, for example, a configuration may be adopted as follows. The information on the change amount of the optical characteristics of the target light flux detected by the optometry unit is acquired by the correction unit which automatically receives the information on the change amount of the optical characteristics of the target light flux.

<Application Example>

Hereinafter, a configuration of the subjective optometry apparatus according to an application example will be described. A configuration in which the subjective optometry apparatus according to this application example includes the projection optical system and the housing will be described as an example. For example, FIGS. 1A and 1B are perspective views illustrating the subjective optometry apparatus 1 when viewed from the front surface side. For example, FIG. 2 is a perspective view illustrating the subjective optometry apparatus 1 according to this application example when viewed from the rear surface side. In this application example, description will be made in such a way that a side on which a presentation window 3 (to be described later) is positioned is set as the front surface of the subjective optometry apparatus 1 and a side on which an observation window 41 (to be described later) is positioned is set as the rear surface of the subjective optometry apparatus 1. For example, FIG. 1A is a perspective view illustrating the subjective optometry apparatus 1 when viewed from the left side of the front surface. In addition, for example, FIG. 1B is a perspective view illustrating the subjective optometry apparatus 1 when viewed from the right side if the front surface.

For example, the subjective optometry apparatus 1 includes the housing 2, the presentation window 3, the holding unit 4, a first operation unit 8, a second operation unit 9, the projection optical system 10, an observation unit 40, an optometry unit 50, and a measurement optical system 100.

For example, in this application example, an examinee faces the front surface of the housing 2. For example, the housing 2 internally accommodates the projection optical system 10. For example, the presentation window 3 is used to present an examination visual target to an eye of the examinee (hereinafter, referred to as a subject eye). For example, the presentation window 3 transmits the target light flux in the projection optical system 10. Therefore, the target light flux is projected on the subject eye through the presentation window 3. For example, the presentation window 3 is closed with a transparent panel in order to prevent dust from entering. For example, as the transparent panel, a transparent member such as an acrylic resin or a glass plate can be used.

In a case where the optometry unit 50 is located between the presentation window 3 and the subject eye, the target light flux is projected on the subject eye through the presentation window 3 and the examination window 53 of the optometry unit 50.

Figure 10:
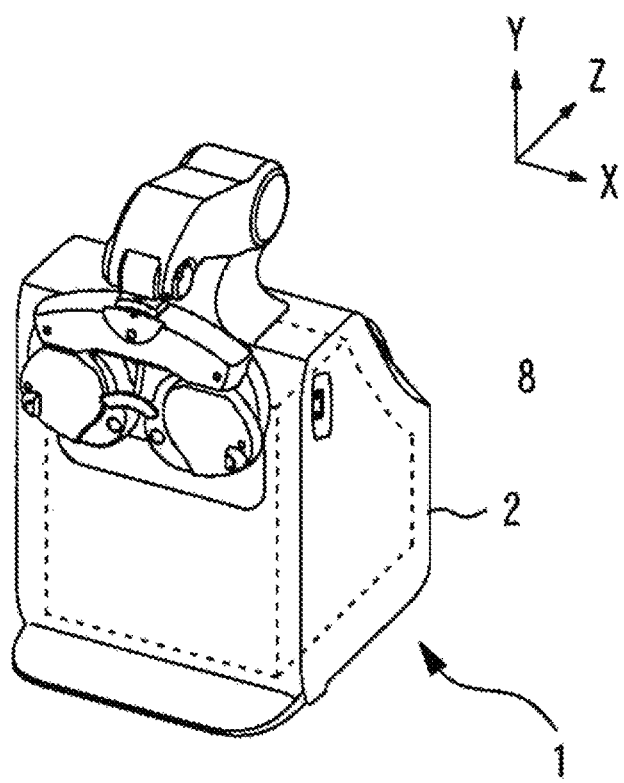
FIG. 10 is a view illustrating a state where a subjective examination using the optometry unit is available.

For example, the holding unit 4 holds the optometry unit 50. For example, the holding unit 4 supports the optometry unit 50 at a retracted position or an examination position. For example, as illustrated in FIGS. 1A and 1B, the retracted position in this application example is in a state where the optometry unit 50 is raised to an upper portion of the housing 2. In addition, as illustrated in FIG. 10, the examination position in this application example is a state where the optometry unit 50 is lowered to the front surface of the housing 2. The retracted position and the examination position are switched by a movement unit (not illustrated) of the holding unit 4 to move a holding arm (not illustrated) of the holding unit 4 upward and downward.

<First Operation Unit and Second Operation Unit>

Hereinafter, the first operation unit 8 and the second operation unit 9 will be described. For example, the first operation unit 8 is an upward-downward movement switch (movement switch of the optometry unit 50). In addition, for example, the second operation unit 9 is an upward-downward movement switch (movement switch of the optometry unit 50). That is, in this application example, the first operation unit 8 and the second operation unit 9 are the operation units for performing the same operation. For example, the first operation unit 8 or the second operation unit 9 is operated. In this manner, the optometry unit 50 can be moved between the examination position in front of the subject eye and the retracted position.

For example, the first operation unit 8 is located on the left side surface of the housing 2. For example, the second operation unit 9 is located on the right side surface of the housing 2. For example, the first operation unit and the second operation unit are arranged above the right and left side surfaces. In this application example, for example, the first operation unit and the second operation unit are arranged at right and left symmetrical positions, based on the center of the housing 2.

In this application example, for example, the first operation unit 8 and the second operation unit 9 are the operation units having the same shape. For example, the first operation unit 8 and the second operation unit 9 have the same shape. Accordingly, when one of the first operation unit 8 or the second operation unit 9 is operated, the subjective optometry apparatus 1 can be operated by performing an operation similar to the other operation. Therefore, it is possible to prevent a possibility that an examiner may perform an incorrect operation, and thus, the subjective optometry apparatus 1 is likely to be operated.

In this application example, as the operation unit for moving the optometry unit 50 between the examination position in front of the subject eye and the retracted position, a configuration having the first operation unit 8 and the second operation unit 9 has been described. However, the present disclosure is not limited thereto. For example, as the operation unit for moving the optometry unit 50 between the examination position in front of the subject eye and the retracted position, a configuration having at least one or more operation units may be adopted. As an example, in a case of using one operation unit, the operation unit may be located at a position where the operation can be performed from the right and left sides of the subjective optometry apparatus 1.

<Projection Optical System>

Figure 3A:
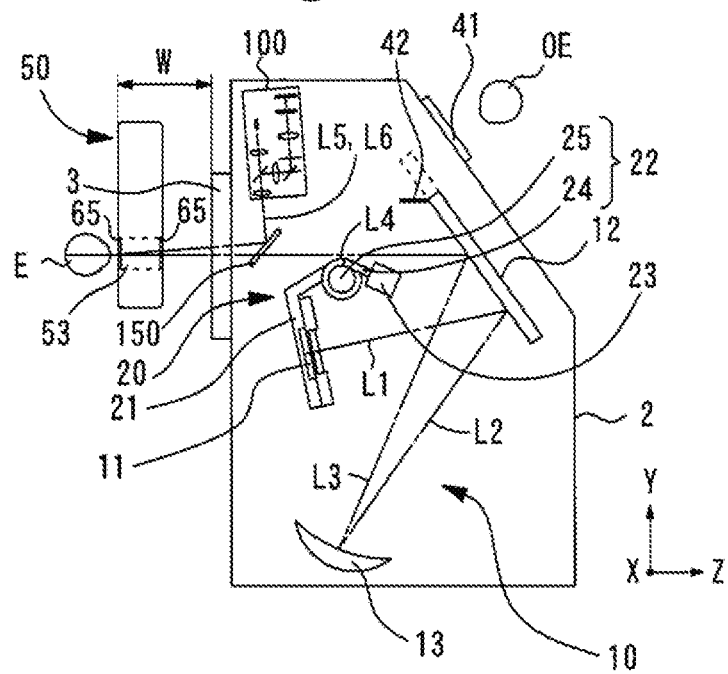
FIGS. 3A and 3B are views illustrating a projection optical system when viewed from a left side surface.
Figure 3B:
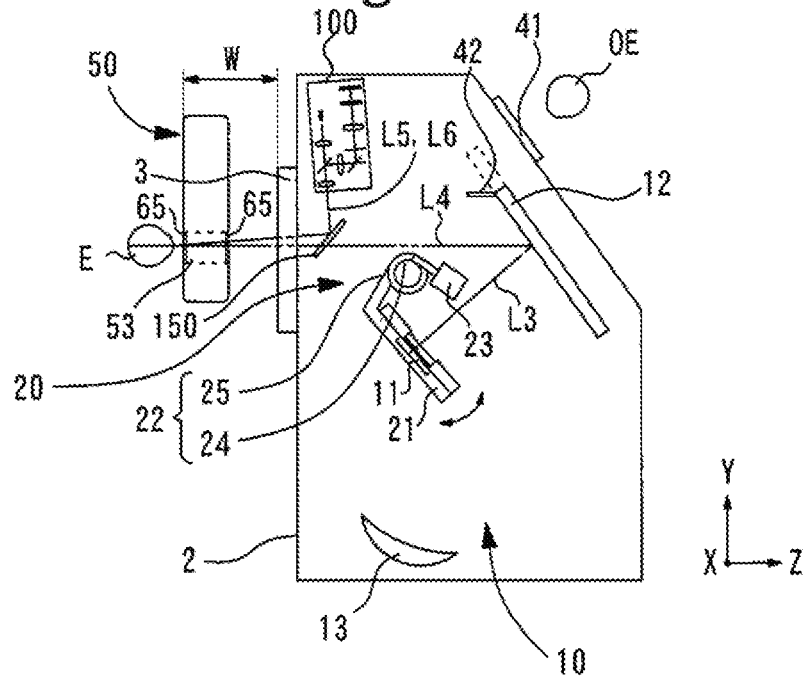

The projection optical system 10 will be described below. For example, FIGS. 3A and 3B are views illustrating the projection optical system 10 when the projection optical system 10 is viewed from the left side surface (arrow direction C1 in FIGS. 1A and 1B). FIG. 3A illustrates an optical arrangement at the time of a far distance examination. FIG. 3B illustrates an optical arrangement at the time of a near distance examination. For example, the projection optical system 10 has the visual target presenting portion, and projects the target light flux emitted from the visual target presenting portion on a subject eye E. For example, in this application example, a display (for example, a display 11) is used as the visual target presenting portion. For example, the projection optical system 10 includes the display 11, the flat mirror 12, the concave mirror 13, and a far-near distance switching unit 20.

For example, the display 11 displays the examination visual target such as a Landolt ring visual target and a fixation visual target. For example, the display on the display 11 is controlled by a control unit 80 (to be described later). For example, as the display, a liquid crystal display (LCD), an organic electro luminescence (EL), and a plasma display may be used.

For example, at the time of the far distance examination illustrated in FIG. 3A, a screen of the display 11 is directed rearward of the housing 2, and the target light flux is output in a rearward direction. The target light flux may be output from the display in a horizontal direction (Z-direction), or may be output in an oblique direction (YZ-direction). For example, at the time of the near distance examination illustrated in FIG. 3B, the screen of the display 11 is directed upward, and the target light flux is output in an upward direction. The target light flux may be output from the display in a vertical direction (Y-direction), or may be output in the oblique direction (YZ-direction). In this way, the target light flux output from the display 11 is projected on the subject eye E.

For example, the flat mirror 12 reflects the target light flux from the display 11, and guides the target light flux to the concave mirror 13. In addition, for example, the flat mirror 12 reflects the target light flux from the display 11, and guides the target light flux to the subject eye E. For example, only a lower portion (solid line portion of the flat mirror 12 in FIGS. 3A and 3B) of the flat mirror 12 is subjected to mirror coating, and an upper portion (dotted line portion of the flat mirror 12 in FIGS. 3A and 3B) of the flat mirror 12 is not subjected to the mirror coating.

Therefore, in this application example, the upper portion of the flat mirror 12 is configured to be transparent. For example, a focal distance of the flat mirror 12 at the time of the near distance examination is designed so that an optical distance from the display to the subject eye E is 40 cm. In this application example, as long as the target light flux can be reflected, this application example is not limited to the configuration using the flat mirror. For example, any reflection member may be used. In this case, for example, a configuration using a prism, a beam splitter, or a half mirror may be adopted.

For example, the concave mirror 13 reflects the target light flux from the display 11 toward the flat mirror 12. For example, in the concave mirror 13, a presentation distance of the examination visual target displayed on the display 11 is set to a far distance examination distance. For example, the focal distance of the concave mirror 13 is designed so that the optical distance from the display 11 to the subject eye E is 5 m. This application example is not limited to the configuration using the concave mirror 13. For example, any reflection member which can reflect the target light flux may be used. In this case, for example, a configuration using an aspheric mirror or a free curved surface mirror may be adopted. In addition, for example, a configuration using the lens may be adopted. In this case, for example, a configuration may be adopted as follows. The target light flux is projected on the subject eye E from the display 11 through the lens. In this manner, the optical distance from the display 11 to the subject eye E is designed to be 5 m.

For example, a beam splitter 150 transmits the target light flux from the display 11 reflected on the flat mirror 12, and guides the target light flux to the subject eye E. In addition, for example, the beam splitter 150 reflects the measurement light output from the measurement light source 130 of the measurement optical system 100 (to be described later), and guides the measurement light to the subject eye E.

For example, at the time of the far distance examination illustrated in FIG. 3A, the target light flux output from the display 11 and passing through the optical members of the flat mirror 12, the concave mirror 13, the flat mirror 12, and the beam splitter 150 in this order is projected on the subject eye E. That is, if the target light flux output from the display 11 is incident on the flat mirror 12 through an optical axis L1, the target light flux is reflected in a direction of an optical axis L2, and is guided to the concave mirror 13. If the target light flux is incident on the concave mirror 13, the target light flux is reflected in a direction of an optical axis L3, and is guided to the flat mirror 12. Furthermore, if the target light flux is incident on the flat mirror 12, the target light flux is reflected in a direction of an optical axis L4, passes through the beam splitter 150, and is projected on the subject eye E of the examinee. In addition, for example, at the time of the near distance examination illustrated in FIG. 3B, the target light flux output from the display 11 and reflected on the flat mirror 12 passes through the beam splitter 150, and is projected on the subject eye E of the examinee. That is, the target light flux output from the display 11 is incident on the flat mirror 12 through the optical axis L3, is reflected in the direction of the optical axis L4, and is projected on the subject eye E of the examinee through the beam splitter 150. For example, in this way, the projection optical system 10 emits the target light flux from the inside to the outside of the housing 2.

For example, the far-near distance switching unit 20 is used in order to switch between a far distance examination optical path at the time of the far distance examination and a near distance examination optical path at the time of the near distance examination. For example, in the far distance examination optical path, the target light flux output from the display 11 is projected on the subject eye through the concave mirror 13 so that the target light flux is projected on the subject eye at the far distance examination distance. In addition, for example, in the near distance examination optical path, an image of the target light flux output from the display 11 is projected on the subject eye at the near distance examination distance without interposing the concave mirror 13 therebetween.

For example, the far-near distance switching unit 20 changes a position of the display 11 at the time of the far distance examination and at the time of the near distance examination. For example, the far-near distance switching unit 20 includes a holding unit 21, a gear 22, and a motor 23. For example, the holding unit 21 holds the display 11. For example, the gear 22 has a worm portion 24 and a wheel portion 25. For example, the worm portion 24 and the wheel portion 25 are formed using gears meshing with each other. For example, the motor 23 is linked to the worm portion 24, and the holding unit 21 is linked to the wheel portion 25. For example, as the motor 23 is driven, the worm portion 24 is rotated. In response thereto, the wheel portion 25 is rotated in an arrow direction. In this manner, the display 11 can be moved integrally with the holding unit 21, and the presentation position of the examination visual target displayed on the screen of the display 11 can be switched at the time of the far distance examination and at the time of the near distance examination. The gear 22 and the motor 23 are arranged on the side wall of the housing 2, and are arranged at positions which do not interfere with the target light flux guided from the display 11 to the subject eye E.

In this application example, a configuration in which the optical axis L3 and the optical axis L4 of the projection optical system 10 are coaxial with each other at the time of the far distance examination and at the time of the near distance examination has been described as an example. However, this application is not limited thereto. For example, in this application example, any configuration may be adopted as long as the target light flux can be guided to the subject eye E. Alternatively, the target light flux may pass through mutually different optical paths at the time of the far distance examination and at the time of the near distance examination.

<Measurement Optical System>

Figure 4:
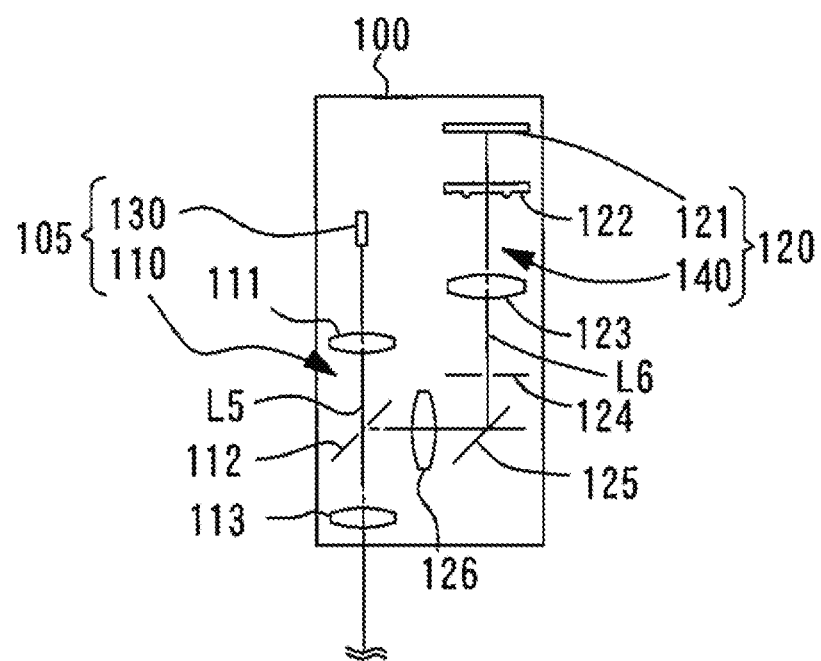
FIG. 4 is a view for describing a measurement optical system.

FIG. 4 is a view for describing a configuration of the measurement optical system 100. Hereinafter, the measurement optical system 100 will be described with reference to FIGS. 3 and 4. For example, the measurement optical system (objective measurement optical system) 100 objectively measures the optical characteristics of the subject eye. For example, the optical characteristics of the subject eye include the eye refractive power, an eye axial length, and a corneal shape. In the present embodiment, an objective measurement unit for measuring the eye refractive power of the subject eye will be described as an example.

For example, the measurement optical system 100 includes a light projecting optical system 105 and a light receiving optical system 120. In the present embodiment, for example, the light projecting optical system 105 includes a measurement light source 130 and an objective optical system 110. As a matter of course, for example, the light projecting optical system 105 may be configured to include only the measurement light source 130. For example, the light receiving optical system 120 includes a light receiving objective optical system 140 and a detector 121 such as a CCD.

For example, in this application example, the measurement optical system 100 outputs the measurement light from the measurement light source 130, and causes the objective optical system 110 to project the spot-like measurement light on the fundus of the subject eye E through the pupil center portion of the subject eye E. For example, the measurement optical system 100 causes the light receiving objective optical system 140 to extract the fundus reflected light reflected from the fundus into a ring shape through the pupil peripheral portion so that the detector 121 detects the ring-shaped fundus reflection image. The measurement optical system 100 is not limited to the above-described configuration. Any configuration may be adopted as long as the measurement optical system has the light projecting optical system which emits the measurement light output from the measurement light source to the fundus of the subject eye and the light receiving optical system which causes the detector to receive the reflected light acquired by the measurement light reflected on the fundus.

For example, the objective optical system 110 includes a relay lens 111, a hole mirror 112, and an objective lens 113 which are arranged on the optical axis L5 of the light projecting optical system 105. For example, the measurement light source 130 is also located on the optical axis L5 of the light projecting optical system 105. For example, the measurement light source 130 is in a conjugate relationship with the fundus of the subject eye, and a hole portion of the hole mirror 112 is in a conjugate relationship with the pupil.

For example, the light receiving objective optical system 140 shares the objective lens 113 and the hole mirror 112 of the objective optical system 110 with the objective optical system 110, and includes a relay lens 126, a mirror 125, a light receiving aperture 124, a collimator lens 123, and a ring lens 122 which are arranged on the optical axis L6 of the light receiving optical system 120 in the reflection direction of the hole mirror 112. For example, the light receiving aperture 124 and the detector 121 are in a conjugate relationship with the fundus of the subject eye. For example, the ring lens 122 is configured to include a lens portion formed in a ring shape and a light blocking portion subjected to light blocking coating in a region other than the lens portion, and is in a conjugate relationship with the pupil of the subject eye. For example, an output from the detector 121 is input to the control unit 80. In this application example, for example, the optical axis L6 of the light receiving optical system 120 is set to be coaxial with the optical axis L5 of the light projecting optical system 105 by the hole mirror 112. As a matter of course, for example, a configuration may be adopted in which the optical axis L6 of the light receiving optical system 120 and the optical axis L5 of the light projecting optical system 105 are not coaxial with each other.

According to the above-described configuration, the measurement light output from the measurement light source 130 is applied to the beam splitter 150 through the relay lens 111, the hole mirror 112, and the objective lens 113. For example, the measurement light applied to the beam splitter 150 is reflected on the beam splitter 150 in the direction of the subject eye E. The measurement light reflected in the direction of the subject eye E forms a spot-like point light source image on the fundus of the subject eye E through an optometry window 53 of the optometry unit 50 and the optical member (for example, the optical member of the lens disc 57 (to be described later)) located in the optometry window. That is, the measurement light is applied to the subject eye along the optical axis L5 of the light projecting optical system 105.

For example, the point light source image applied to the fundus of the subject eye is reflected and scattered, and is emitted to the subject eye E. The point light source image is reflected on the beam splitter 150, and is collected by the objective lens 113. The reflected light collected by the objective lens 113 is reflected on the hole mirror 112 in the direction of the relay lens 126, and is collected again at the position of the light receiving aperture 124 through the relay lens 126 and the mirror 125. The reflected light collected by the light receiving aperture 124 forms a ring-shaped image on the detector 121 with using the collimator lens 123 and the ring lens 122.

As an arrangement position of the measurement optical system 100, the measurement optical system 100 can be located at any desired position. For example, the measurement optical system 100 may be located at any desired position inside the housing 2.

In this case, for example, the measurement optical system 100 may be located on the optical axis L4, at a position where the measurement light is transmitted through the flat mirror 12. In this case, instead of the flat mirror 12, the optical member transmitting the measurement light from the measurement optical system 100 and reflecting the target light flux from the projection optical system 10 (for example, the beam splitter) may be located.

In addition, for example, the measurement optical system 100 may be located at any desired position outside the housing 2. For example, the measurement optical system 100 may be located in the optometry unit 50. In this case, for example, the optometry unit 50 may be located at a position between the housing 2 and the optometry unit 50. For example, in a case where the optometry unit 50 is located in the optometry unit 50, the position of the measurement optical system 100 can be easily adjusted in accordance with the position adjustment of the optometry unit 50. As an example, for example, in a case where the measurement optical system 100 is disposed in each of the right and left examination windows 53 of the optometry unit 50 so as to change the position of the right and left examination windows 53 in the optometry unit 50 in accordance with a distance between the pupils of the examinee, the measurement optical system 100 is moved along with the movement (constantly in response to the movement) of the examination windows 53 of the optometry unit 50. Accordingly, the position can be easily adjusted.

For example, in this application example, the optical axis L5 of the light projecting optical system 105 (in this application example, the optical axis of the measurement light source 130 and of the objective optical system 110) and the optical axis L5 of the light receiving optical system 120 are arranged to be coaxial with each in the middle of the optical path. However, the application example is not limited to this configuration.

For example, the light projecting optical system 105 and the light receiving optical system 120 may be separately arranged at mutually different positions so that the measurement is performed using mutually different optical axes. In this case, for example, the light projecting optical system 105 and the light receiving optical system 120 may be arranged at mutually different positions inside the housing 2. In addition, in this case, for example, the light projecting optical system 105 and the light receiving optical system 120 may be arranged at different positions outside the housing 2. In addition, in this case, for example, one of the light projecting optical system 105 and the light receiving optical system 120 may be located inside the housing 2 and the other may be located outside the housing 2.

<Observation Unit>

Figure 5:
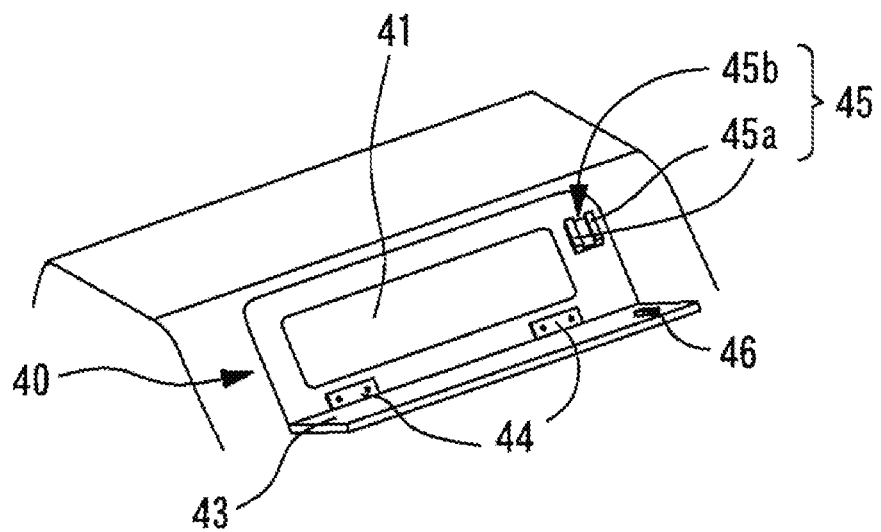
FIG. 5 is a view for describing an observation unit.

Hereinafter, the observation unit 40 will be described. FIG. 5 is a view for describing the observation unit 40. For example, the observation unit 40 in this application example is used in order to observe a positional relationship (to be described later) between the optometry unit 50 and the subject eye E through the presentation window 3. For example, in this application example, the observation unit 40 includes an observation window 41, a shield portion 42, a cover 43, and a detector (detection unit) 45. The observation unit 40 may be configured to include at least the observation window 41.

For example, the observation window 41 is used in order to observe the positional relationship between the optometry unit 50 and the subject eye E from outside the housing 2 through the presentation window 3. For example, the observation window 41 in this application example is located at a position where an examiner's eye OE can confirm the pupil position of the subject eye E. For example, in a case where the examiner looks into the observation window 41, the flat mirror 12 is formed to be transparent in a region through which the examiner's line of sight passes so that the examiner's line of sight is not blocked by the flat mirror 12. For example, the shield portion 42 prevents the target light flux output from the projection optical system 10 from entering the observation window 41. For example, in this application example, the shield portion 42 is located at a boundary between a transparent portion and a mirror portion in the flat mirror 12.

For example, the cover 43 is fixed to the housing 2 by a hinge 44, and can be opened and closed with respect to the observation window 41. For example, the cover 43 can be opened and closed by the examiner who pushes and pulls a knob (not illustrated).

For example, the detector 45 detects the opening and closing of the cover 43 in the observation unit 40. For example, the detector 45 is configured to use an optical sensor such as a photo interrupter. That is, the detector 45 in this application example has a projection portion 45a in which a light emitting element and a light receiving element face each other, and a protruding portion 46 disposed in the cover 43 is fitted into a recess portion 45b. For example, if the light from the light emitting element is blocked by the protruding portion 46 fitted to the recess portion 45b, the detector 45 detects that the cover is in a closed state. In addition, for example, if the protruding portion 46 is separated from the recess portion 45b and the light from the light emitting element is received by the light receiving element, the detector 45 detects that the cover is in an open state.

<Optometry Unit>

Hereinafter, the optometry unit 50 will be described. For example, the optometry unit 50 is close to the housing 2 (refer to FIGS. 3A and 3B). For example, in this application example, a distance W (refer to FIGS. 3A and 3B) from the examination window 53 (dotted line portion in FIGS. 3A and 3B) in the optometry unit 50 to the presentation window 3 located in the housing 2 is designed to be approximately 135 mm. The distance W from the examination window 53 to the presentation window 3 is not limited to this application example. For example, in a case where the distance W is shorter than a head length of the examiner, the examiner cannot insert his or her head between the optometry unit 50 and the housing 2. Accordingly, the examiner is less likely to observe the positional relationship between the optometry unit 50 and the subject eye E. Therefore, in a case where the distance W is shorter than the head length of the examiner, the observation window 41 can be effectively used.

For example, the optical member is located in the examination window 53. In this application example, the examination window 53 has protective covers 65 as the optical members. For example, the protective covers 65 are used in order to protect the other optical member located in the examination window 53. For example, the protective covers 65 are respectively fixed and located on the subject eye E side and the housing 2 side in the optometry window 53 of the optometry unit 50.

Figure 6:
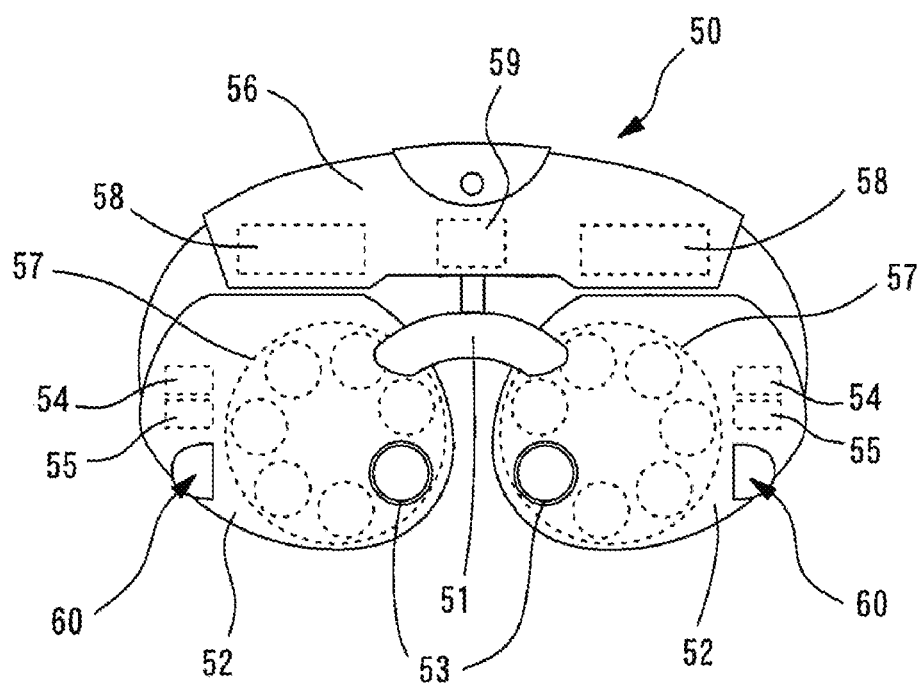
FIG. 6 is a view illustrating an optometry unit.

For example, FIG. 6 is a view illustrating the optometry unit 50. For example, the optometry unit 50 includes a forehead band 51, a pair of right and left lens chamber units 52, the examination window 53, a drive unit 54, a drive unit 55, a movement unit 56, and a corneal position aligning optical system 60. For example, the forehead band 51 comes into contact with the forehead of the examinee, and is used in order to maintain a constant distance between the subject eye E and the optometry unit 50.

For example, the lens chamber unit 52 is located in the examination window 53 so as to switch the optical members. For example, the lens disc 57 is included inside the lens chamber unit 52. In the lens disc 57, multiple optical members (spherical lens, cylinder lens, and dispersive prism) are arranged on the same circumference. For example, the lens disc 57 is rotationally controlled by the drive unit 54 (actuator). In this manner, the optical members desired by the examiner are arranged in the examination window 53. For example, the optical members arranged in the examination window 53 are rotationally controlled by the drive unit 55 (motor or solenoid). In this manner, the optical members are arranged in the examination window 53 at a rotation angle desired by the examiner.

For example, the lens disc 57 is formed using one lens disc or a plurality of lens discs. For example, in a case where the plurality of lens discs (lens disc group) are provided, drive units corresponding to the respective lens discs are respectively provided. For example, the respective lens discs of the lens disc group include an aperture (or a lens of 0D) and a plurality of optical members. As a type of each lens disc, a spherical lens disc having a plurality of spherical lenses having different degrees of power, a cylinder lens disc having a plurality of cylinder lenses having different degrees of power, and an auxiliary lens disc are representatively used. In addition, the lens disc in this application example includes an alignment lens having crosshairs. For example, the auxiliary lens disc has at least one of a red filter/green filter, a prism, a cross cylinder lens, a polarizer, a Maddox lens, and an auto cross cylinder lens. For a detailed configuration of the lens disc, refer to JP-A-2007-68574 and JP-A-2011-72431.

For example, the movement unit 56 adjusts an interval between the lens chamber units 52. For example, the interval between the right and left lens chamber units is adjusted by the drive unit 58 having a slide mechanism. In this manner, the interval between the examination windows 53 can be changed in accordance with PD of the subject eye. In addition, the movement unit 56 adjusts a convergence angle (inset angle) of the right and left lens chamber units. For example, the convergence angle of the right and left optometry units is adjusted by the drive unit 59 having a convergence mechanism. In addition, for a detailed configuration of the movement unit, refer to JP-A-2004-329345.

The optometry unit 50 is not limited to the above-described configuration. For example, the optometry unit 50 may be configured to change the optical characteristics (for example, at least one of the spherical power, the cylindrical power, the cylindrical axis, the polarization characteristics, and the aberration amount) of the target light flux. For example, as a configuration for changing the optical characteristics of the target light flux, a configuration for controlling the optical member may be adopted. For example, a configuration using the wavefront modulation element and the variable focus lens may be adopted.

For example, in this application example, as the distance changing optical member, the lens disc 57 (optical member of the lens disc 57) of the optometry unit 50 is used. That is, for example, in this application example, the configuration of the optometry unit 50 is also used as the distance changing optical member for changing the examination distance and a correction unit for changing the optical characteristics of the target light flux. In this case, for example, the lens disc 57 is driven by driving at least one of the drive unit 54 and the drive unit 55. That is, the distance changing optical member is driven by driving at least one of the drive unit 54 and the drive unit 55.

In this application example, a configuration in which the configuration of the symmetry unit 50 is also used as the distance changing optical member has been described as an example. However, the application example is not limited thereto. A dedicated distance changing optical member may be separately provided, or another optical member in the projection optical system 10 may be shared in use. In this application example, for example, the distance changing optical member includes an example of a configuration in which the distance changing optical member is located between the flat mirror 12 and the subject eye. As a matter of course, an arrangement position of the distance changing optical member is not limited to the above-described position as long as the examination distance can be optically changed.

<Off-Axis Configuration>

Here, for example, in this application example, the optical axis L5 of the light projecting optical system 105 and the optical axis L6 of the light receiving optical system 120 are set to be off-axis from the optical axis of the optical member of the optometry unit 50. For example, in this application example, the optical axis L5 of the light projecting optical system 105 is set to be off-axis from the optical axis of the optical member of the lens disc 57 located in the examination window 53 of the optometry unit 50. In addition, for example, in this application example, the optical axis L6 of the light receiving optical system 120 is set to be off-axis from the optical axis of the optical member of the lens disc 57 located in the examination window 53 of the optometry unit 50. In addition, in this application example, the optical axis L5 of the light projecting optical system 105 and the optical axis L6 of the light receiving optical system 120 are set to be coaxial with each other from the middle of the optical path.

In this application example, the optical axis L5 of the light projecting optical system 105 and the optical axis L6 of the light receiving optical system 120 are set to be off-axis from the optical axis of the optical member of the optometry unit 50. However, this application example is not limited thereto. For example, a configuration may be adopted as follows. At least one of the optical axis L5 of the light projecting optical system 105 and the optical axis L6 of the light receiving optical system 120 is set to be off-axis from the optical axis of the optical member of the optometry unit 50. In this case, for example, a configuration may be adopted as follows. Only the optical axis L5 of the light projecting optical system 105 out of the optical axis L5 of the light projecting optical system 105 and the optical axis L6 of the light receiving optical system 120 is set to be off-axis from the optical axis of the optical member of the optometry unit 50. In addition, in this case, for example, only the optical axis L6 of the light receiving optical system 120 out of the optical axis L5 of the light projecting optical system 105 and the optical axis L6 of the light receiving optical system 120 is set to be off-axis from the optical axis of the optical member of the optometry unit 50. In addition, in this case, for example, a configuration may be adopted as follows. Both the optical axis L5 of the light projecting optical system 105 and the optical axis L6 of the light receiving optical system 120 are set to be off-axis from the optical axis of the optical member of the optometry unit 50. In a case where both the optical axis L5 of the light projecting optical system 105 and the optical axis L6 of the light receiving optical system 120 are set to be off-axis from the optical axis of the optical member of the optometry unit 50, the optical axis L5 of the light projecting optical system 105 and the optical axis L6 of the light receiving optical system 120 may be coaxial with each other, or may be mutually different axes. In a case where both axes are coaxial with each other, both the axes may be configured to be completely coaxial with each other, or may be configured to be coaxial with each other in the middle of the optical path.

For example, as illustrated in FIGS. 3A and 3B, in this application example, for example, the optical axis L5 of the light projecting optical system 105 and the optical axis L6 of the light receiving optical system 120 are arranged to be inclined from the optical axis of the optical member of the lens disc 57 located in the examination window 53 of the optometry unit 50. In this manner, the optical axis L5 of the light projecting optical system 105 and the optical axis L6 of the light receiving optical system 120 are set to be off-axis from the optical axis of the optical member of the lens 57 located in the examination window 53 of the optometry unit 50.

In this application example, the following configuration has been described as an example. In addition to the optical axis L5 of the light projecting optical system 105, the optical axis L6 of the light receiving optical system 120 is also inclined from the optical axis of the optical member of the optometry unit 50. However, this application example is not limited thereto. For example, a configuration may be adopted as follows. At least one of the optical axis L5 of the light projecting optical system 105 and the optical axis L6 of the light receiving optical system 120 is inclined from the optical axis of the optical member of the optometry unit 50. As an example, for example, the optical axis L5 of the light projecting optical system 105 may be set to be coaxial with the optical axis of the optical member of the optometry unit 50. In addition, as an example, for example, the optical axis L6 of the light receiving optical system 120 may be set to be coaxial with the optical axis of the optical member of the optometry unit 50.

In this application example, the measurement light source 130 and the objective optical system 110 are arranged on the optical axis L5 of the light projecting optical system 105. That is, in this application example, the optical axis of the measurement light source 130 and the optical axis of the objective optical system 110 are illustrated as the optical axis L5. In addition, the detector 121 and the light receiving objective optical system 140 are arranged on the optical axis L6 of the light receiving optical system 120. That is, in this application example, the optical axis of the detector 121 and the optical axis of the light receiving objective optical system 140 are illustrated as the optical axis L5.

In this application example, the following configuration has been described as an example. The light projecting optical system 105 includes the measurement light source 130 and the objective optical system 110, and the optical axis of the measurement light source 130 and the optical axis of the objective optical system 110 are set to be off-axis from the optical axis of the optical member of the optometry unit 50. However, this application example is not limited thereto. For example, in a case where the light projecting optical system 105 includes only the measurement light source 130, the optical axis of the measurement light source 130 is set to be off-axis from the optical axis of the optical member of the optometry unit 50. In this manner, the optical axis L5 of the light projecting optical system 105 may be set to be off-axis from the optical axis of the optical member of the optometry unit 50. In addition, for example, in a case where the light projecting optical system 105 includes the measurement light source 130 and the objective optical system 110, one of the measurement light source 130 and the objective optical system 110 is set to be off-axis from the optical axis of the optical member of the optometry unit 50. In this manner, the optical axis L5 of the light projecting optical system 105 may be set to be off-axis from the optical axis of the optical member of the optometry unit 50.

In this application example, the optical axis of the optical member of the lens disc 57 located in the examination window 53 of the optometry unit 50 is set to be coaxial with the optical axis L4 of the projection optical system 10. That is, the optical axis (optical axis of the optical member of the optometry unit 50) of the optical member of the lens disc 57 located in the examination window 53 of the optometry unit 50 is coaxial with the visual axis set for the subject eye to view the target light flux from the projection optical system 10, which is projected in the frontal direction, and is illustrated by the optical axis L4.

In this application example, for example, in the optical axis L5 of the light projecting optical system 105, the optical axis L5 of the light projecting optical system 105 (in this application example, the measurement light source 130 and the objective optical system 110) is inclined from the optical axis (in this application example, the optical axis L4) of the optical member of the lens disc 57 located in the examination window 53 of the optometry unit 50 so that the optical axis L5 is off-axis from the optical axis L4 (visual axis). In addition, in this application example, for example, the optical axis L6 of the light receiving optical system 120 is inclined from the optical axis of the optical member of the lens disc 57 located in the examination window 53 of the optometry unit 50 so that the optical axis L6 of the light receiving optical system 120 is off-axis from the optical axis L4 (visual axis). For example, one of the optical axis L5 of the light projecting optical system 105 and the optical axis L6 of the light receiving optical system 120 may be set to be coaxial with the visual axis (optical axis L4), and the optical axis of the optical member of the optometry unit 50 may be inclined from at least one optical axis of the optical axis L5 of the light projecting optical system 105 and the optical axis L6 of the light receiving optical system 120.

In this application example, as the off-axis configuration, the following configuration has been described as an example. The optical axis L5 of the light projecting optical system 105 and the optical axis L6 of the receiving optical system 120 are inclined from the light axis (optical axis L4) of the optical member of the optometry unit 50. However, this application example is not limited thereto. For example, as the off-axis configuration, a configuration may be adopted as follows. The optical axis L5 of the light receiving optical system 105 and the optical axis L6 of the light receiving optical system 120 are eccentric so as to be off-axis from the optical axis (optical axis L4) of the optical member of the optometry unit 50. In this case, for example, the optical axis of the optical unit 50 may be coaxial with the visual axis (optical axis L4), and the optical axis L5 of the light projecting optical system 105 and the optical axis L6 of the light receiving optical system 120 may be eccentric from the optical axis of the optical member of the optometry unit 50. In addition, in this case, for example, the optical axis L5 of the light projecting optical system 105 and the optical axis L6 of the light receiving optical system 120 may be coaxial with the visual axis (optical axis L4), and the optical axis of the optical member of the optometry unit 50 may be eccentric from the optical axis L5 of the light projecting optical system 105. In addition, in this case, for example, one of the optical axis L5 of the light projecting optical system 105 and the optical axis L6 of the light receiving optical system 120 may be coaxial with the visual axis (optical axis L4), and the optical axis of the optical member of the optometry unit 50 may be eccentric from at least one optical axis of the optical axis L5 of the light projecting optical system 105 and the optical axis L6 of the light receiving optical system 120. As a matter of course, a configuration may be adopted as follows. The optical axis of the optical member of the optometry unit 50 may be in a relationship of being off-axis from at least one optical axis of the optical axis L5 of the light projecting optical system 105 and the optical axis L6 of the light receiving optical system 120. The optical axis of the optical member of the optometry unit 50, the optical axis L5 of the light projecting optical system 105, and the optical axis L6 of the light receiving optical system 120 may be eccentric from the visual axis (optical axis L4).

Also, for example, in the off-axis configuration, a configuration may be adopted in which one optical axis of the optical axis L5 of the light projecting optical system 105 and the optical axis L6 of the light receiving optical system 120 is inclined and the other optical axis is eccentric.

Figure 7:
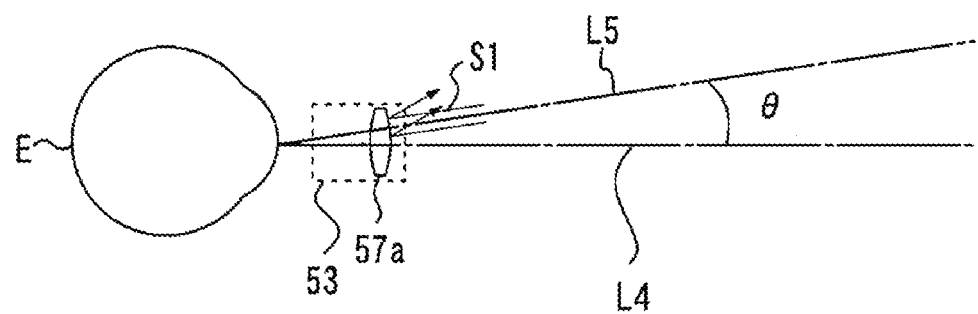
FIG. 7 is a view for describing an inclination configuration.
Figure 8:
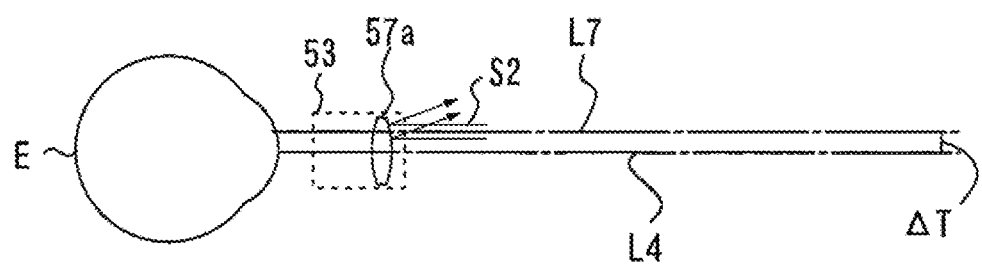
FIG. 8 is a view for describing an eccentricity configuration.

Here, the off-axis configuration will be described in detail. For example, FIG. 7 is a view for describing an inclination configuration in this application example. FIG. 8 is a view for describing an eccentricity configuration which is a modification example. Referring to FIGS. 7 and 8, a case where a lens 57a is located as the optical member located in the optometry window 53 of the optometry unit 50 will be described as an example. As a matter of course, for example, a configuration may be adopted in which a plurality of lenses are provided as the optical member located in the optometry window 53 of the optometry unit 50. In addition, in FIGS. 7 and 8, the optical axis L5 of the light projecting optical system 105 will be described as an example. However, the optical axis L6 of the light receiving optical system 120 can be similarly described. Therefore, the optical axis L6 of the light receiving optical system 120 will be omitted in the description.

For example, FIG. 7 illustrates a state where the optical axis L5 of the light projecting optical system 105 is inclined at an angle θ from the optical axis of the optical member of the optometry unit 50. In this application example, the optical axis of the optical member of the optometry unit 50 is coaxial with the visual axis (optical axis L4 of the projection optical system 10). Therefore, the optical axis of the optical member of the optometry unit 50 will be described as the optical axis L4. For example, the optical axis L5 is inclined from the optical axis L4. Accordingly, in the off-axis state of the optical axis L4, the measurement light from the light projecting optical system 105 is applied to the subject eye E through the optical member located in the examination window 53 of the optometry unit 50. In addition, the reflected light of the measurement light reflected on the subject eye E is detected by the detector 121 of the light receiving optical system 120 along the optical axis L5 and the optical axis L6.

For example, in a case where the optical axis L5 is coaxial with the optical axis L4 (case where the optical axis of the optical member of the optometry unit 50 and the optical axis of the objective optical system 110 are coaxial with each other), the reflected light reflected on the optical member in addition to the reflected light reflected on the subject eye E is detected by the light receiving optical system 120. As illustrated in FIG. 7, for example, the optical axis L5 is inclined from the optical axis L4. In this manner, reflected light S of the measurement light reflected on the lens surface of the lens 57a is directed in a direction deviating from a region detected by the light receiving optical system 120. The reflected light S1 of the measurement light reflected on the lens surface is reflected in the direction deviating from the region detected by the light receiving optical system 120. However, the measurement light reflected on the fundus of the subject eye is reflected in various directions as diffused light. Accordingly, the reflected light from the fundus can be detected by the light receiving optical system 120. In this manner, the reflected light of the lens 57a can be prevented from being detected by the light receiving optical system 120. In this application example, the reflection on the front surface side (housing side) of the lens 57a has been described as an example. However, the reflection on the rear surface side (examinee side) of the lens 57a can be similarly prevented.

For example, FIG. 8 illustrates a state where the optical axis L7 of the light projecting optical system 105 is eccentric as much as a shift amount ΔT from the optical axis of the optical member of the optometry unit 50. As illustrated in FIG. 8, for example, since the optical axis L7 is eccentric from the optical axis L4, reflected light S2 reflected on the lens surface of the lens 57a deviates from the region detected by the light receiving optical system 120. In this manner, the reflected light of the lens 57a can be prevented from being detected by the light receiving optical system 120.

In this way, for example, the subjective optometry apparatus includes the measurement optical system that objectively measures the optical characteristics of the subject eye, and the optical axis of the measurement optical system is set to be off-axis from the optical axis of the optical member in the optometry unit. In this manner, the measurement light of the light projecting optical system is reflected on the optical member of the optometry unit. Consequently, the reflected light from the optical member of the optometry unit is detected together with the reflected light reflected on the subject eye. Accordingly, it is possible to prevent a possibility that the optical characteristics of the subject eye cannot be satisfactorily measured. That is, the reflected light from the optical member of the optometry unit is prevented from being detected by the detector. In this manner, it is possible to prevent a possibility that the optical characteristics of the subject eye cannot be satisfactorily measured.

In addition, for example, the optical axis of the optical member in the optometry unit may be coaxial with the visual axis set for the subject eye to view the target light flux which is projected in the frontal direction. The light projecting optical system may be located so that the optical axis of the light projecting optical system is off-axis from the optical axis of the optical member in the optometry unit. In this manner, compared to a configuration in which the visual axis and the optical axis of the light projecting optical system are coaxial with each other, and in which the optical member of the optometry unit is located so that the optical axis of the optical member of the optometry unit is set to be off-axis from the light projecting optical system, an easier configuration can prevent the reflected light from the optical member of the optometry unit from being detected by the detector.

In addition, for example, the optical axis of the optical member in the optometry unit may be coaxial with the visual axis set for the subject eye to view the target light flux which is projected in the frontal direction. The light receiving optical system may be located so that the optical axis of the light receiving optical system is off-axis from the optical axis of the optical member in the optometry unit. In this manner, compared to a configuration in which the visual axis and the optical axis of the light receiving optical system are coaxial with each other, and in which the optical axis of the optical member of the optometry unit is set to be off-axis from the light receiving optical system, an easier configuration can prevent the reflected light from the optical member of the optometry unit from being detected by the detector.

In this application example, the following configuration has been described as an example. The visual axis (optical axis L4 of the projection optical system 10) and the optical axis of the optical member of the optometry unit 50 are set to be coaxial with each other. The optical axis L5 of the light projecting optical system 105 and the optical axis L6 of the light receiving optical system 120 are inclined from the optical axis of the optical member of the optometry unit 50. However, this application example is not limited thereto. For example, a configuration may be adopted as follows. The visual axis and at least one optical axis of the optical axis L5 of the light projecting optical system 105 and the optical axis L6 of the light receiving optical system 120 may be coaxial with each other, and the optical axis of the optical member of the optometry unit 50 may be inclined from at least one optical axis of the optical axis L5 of the light projecting optical system 105 and the optical axis L6 of the light receiving optical system 120. As a matter of course, a configuration may be adopted as follows. The optical axis of the optical member of the optometry unit 50, and at least one optical axis of the optical axis L5 of the light projecting optical system 105 and the optical axis L6 of the light receiving optical system 120 may be in the off-axis relationship. The optical axis of the optical member of the optometry unit 50, the optical axis L5 of the light projecting optical system 105, and the optical axis L6 of the light receiving optical system 120 may be inclined from the visual axis (optical axis L4 of the projection optical system 10).

In this application example, a configuration in which the optical axis of the optical member of the optometry unit 50 is not inclined has been described as an example. However, this application example is not limited thereto. At least some optical members out of the optical members of the optometry unit 50 may be inclined. In this case, for example, only the protective cover 65 out of the optical members in the optometry unit 50 may be configured to be inclined. In this way, in the optical members of the optometry unit, the protective cover 65 serving as the optical member which is not driven is inclined. In this manner, it is possible to further prevent the reflected light from the optometry unit from being detected by the detector. That is, the protective cover 65 serving as the optical member which is not driven out of the optical members of the optometry unit is inclined. In this manner, an easier configuration can prevent the reflected light from the optometry unit 50 from being detected by the detector.

<Control Unit>

Figure 9:
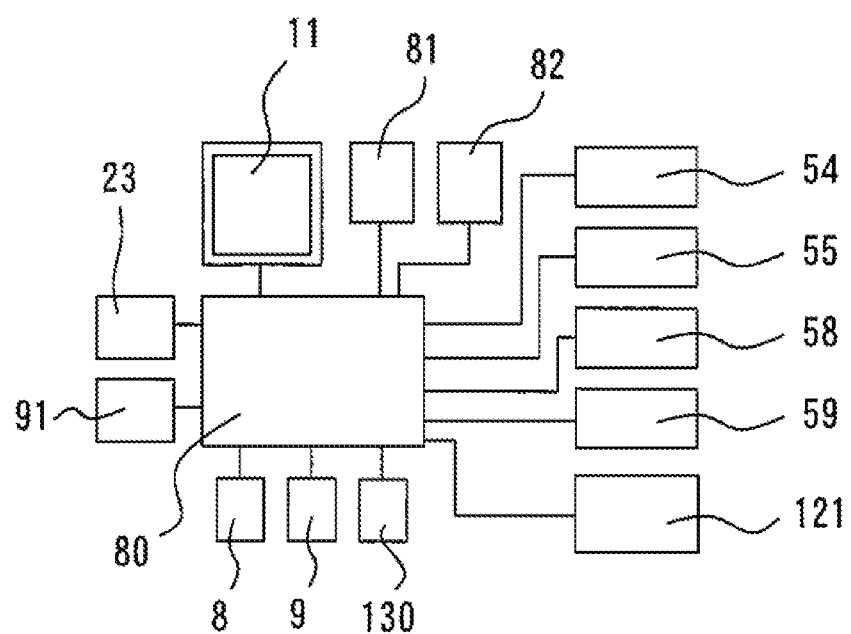
FIG. 9 is a schematic configuration diagram of a control system in the subjective optometry apparatus.

For example, FIG. 9 is a schematic block diagram of a control system in the subjective optometry apparatus 1. For example, the first operation unit 8, the second operation unit 9, the display 11, the detector 45, the controller 81, a nonvolatile memory 82, a light source 91, the detector 121, and a light source 130 are connected to the control unit 80. In addition, for example, a motor included in a movement unit (not illustrated), the motor 23 included in the far-near distance switching unit 20, and drive units (drive units 54, 55, 58, and 59) included in respective members of the optometry unit 50 are connected to the control unit 80.

For example, the control unit 80 includes a CPU (processor), a RAM, and a ROM. For example, the CPU is responsible for controlling each member in the subjective optometry apparatus 1. For example, the RAM temporarily stores various types of information. For example, the ROM stores various programs for controlling the operations of the subjective optometry apparatus 1 or examination visual target data. The control unit 80 may be configured to include a plurality of control units (that is, a plurality of processors).

For example, the controller 81 is used when switching displays of the display 11 in the projection optical system 10 or arrangements of the optical members in the optometry unit 50. For example, a signal input from the controller 81 is input to the control unit 80 via a cable (not illustrated). In this application example, a configuration may be adopted so that the signal from the controller 81 is input to the control unit 80 via wireless communication using infrared.

For example, the nonvolatile memory 82 is a non-transitory storage medium which can hold stored contents even when power supply is shut off. For example, as the nonvolatile memory (hereinafter, referred to as a memory) 82, a hard disk drive, a flash ROM, the subjective optometry apparatus, or a USB memory can be used. For example, the memory 82 stores multiple items of the examination visual target data (for example, visual target data of visual acuity values 0.1 to 2.0) such as Landolt ring visual targets.

In addition, for example, depending on the examination distance to be set and the distance between the pupils of the examinee, the memory 82 stores a table for setting the optical path (optical path of either the far distance examination optical path or the near distance examination optical path), the spherical refractive power (spherical power), and the prism amount (prism power and base direction of the prism) (details will be described later).

For example, in this application example, the control unit 80 switches measurement modes of the subjective optometry apparatus 1, based on a detection result of the detector 45. For example, in this application example, the control unit 80 automatically switches the measurement modes in conjunction with the opening and closing of the cover 43. For example, if the detector 45 detects that the cover 43 is open, the control unit 80 sets the measurement mode to a second mode for confirming the pupil position of the examinee. In addition, for example, if the detector 45 detects that the cover 43 is closed, the control unit 80 sets the measurement mode to a first mode for performing the subjective examination of the examinee. In this application example, a configuration is adopted so that the measurement modes are automatically switched in conjunction with opening and closing of the cover 43. However, this application example is not limited thereto. For example, the measurement modes may be manually switched by the examiner. In this case, a configuration may be adopted in which a signal for switching the measurement modes is input to the control unit 80 with using the controller 81 (to be described later).

For example, in this application example, the control unit 80 switches between a far distance examination mode for performing the subjective examination at the far distance examination distance and a near distance examination mode for performing the subjective examination at the near distance examination distance. For example, the examination modes for changing the examination distance may be manually switched by the examiner. In this case, a configuration may be adopted in which a signal for switching the examination mode is input to the control unit 80 with using the controller 81 (to be described later). As a matter of course, a configuration may be adopted as follows. The examination may be performed sequentially at different examination distances, and the examination modes may be automatically switched.

<Examination Operation>

An examination operation of the subjective optometry apparatus 1 having the above-described configuration will be described. First, for example, the examiner operates the first operation unit 8 so as to lower the optometry unit 50 to an examination position illustrated in FIG. 8. For example, if the first operation unit 8 is operated, the control unit 80 drives the motor 30. For example, a motor (not illustrated) is driven, thereby lowering the optometry unit 50 toward the examination position. For example, if the optometry unit 50 is moved to the examination position by driving the motor (not illustrated), lowering of the optometry unit 50 stops. In this manner, as illustrated in FIG. 10, the eye refractive power measurement unit 50 is completely moved to the examination position, and the subjective optometry apparatus 1 is in a state where the subjective examination and the objective measurement using the optometry unit 50 can be performed.

As described above, the optometry unit 50 is moved to the examination position. Subsequently, for example, the examiner measures the PD of the examinee in advance before performing the subjective examination, and inputs the measured PD in the subjective optometry apparatus 1. In this manner, the control unit 80 drives the drive unit 58, adjusts the interval between the right and left lens chamber units 52, and changes the interval between the examination windows 53 in accordance with the PD of the subject eye. For example, the control unit 80 adjusts the interval so that the distance in the horizontal direction (X-direction) between the optical axes of the right and left examination windows 53 is identical to the PD. In this application example, the term of identical includes substantially identical.

Subsequently, the examiner instructs the examinee to look into the examination window 53. Here, for example, the examiner opens the cover 43 in order to confirm the interpupil distance PD of the subject eye E. In this case, the detector 45 detects that the cover 43 is open, and the control unit 80 switches the measurement mode to the second mode for confirming the pupil position of the examinee.

For example, if necessary, the examiner operates the controller 81 so as to adjust the interval between the right and left lens chamber units 52. Thereafter, the examiner aligns the subject eye E with the optometry unit 50 with using a corneal position aligning optical system 60 in order to confirm a corneal apex position of the subject eye E.

For example, if the subject eye E is completely aligned with the optometry unit 50, the examiner closes the cover 43, and starts the subjective examination and the objective measurement. In this case, the control unit 80 causes the detector 45 to detect that the cover 43 is closed, and switches the measurement mode to the first mode for performing the subjective examination of the examinee.

First, the objective measurement is performed. For example, the examiner operates the controller 81 so as to select a switch for starting the objective measurement. For example, the control unit 80 issues an objective measurement start trigger signal (hereinafter, referred to as a trigger signal) for starting the objective measurement (objective measurement), based on an output of an operation signal output from the controller 81. For example, if the trigger signal for starting the objective measurement is issued, the control unit 80 outputs the measurement light from the measurement light source 130 of the light projecting optical system 105. In this case, the measurement light is emitted to the fundus of the subject eye E through the objective optical system 110 and the beam splitter 150. The reflected light of the measurement light reflected from the fundus is detected by the detector 121 of the light receiving optical system 120 through the beam splitter 150 and the light receiving optical system 120.

For example, the reflected light is detected by the detector 121, and the output signal from the detector 121 is stored in the memory 82 as image data (measurement image). Thereafter, the control unit 80 performs image analysis on the ring image stored in the memory 82 so as to obtain a value of refractive power in each meridian direction. The control unit 80 obtains the objective eye refractive power (objective value) such as the spherical power (S), the astigmatic power (C), and the astigmatic axis angle (A) of the subject eye. The obtained objective value is stored in the memory 82.

For example, if the objective measurement is completely performed, the control unit 80 starts the subjective examination. For example, the control unit 80 sets the optical characteristics of the subject eye measured through the objective measurement, as an initial value of the subjective examination. For example, in this application example, as the optical characteristics used for setting the initial value, the eye reflective power (for example, the spherical power, the astigmatic power, and the astigmatic axis angle) will be described as an example. In this application example, as the optical characteristics used for setting the initial value, the eye refractive power will be described as an example. However, but this application example is not limited thereto. For example, as the optical characteristics used for setting the initial value, different optical characteristics may be used. In addition, for example, as the eye refractive power used for setting the initial value, at least one of the spherical power, the astigmatic power, and the astigmatic axis angle may be used.

For example, in this application example, the control unit 80 retrieves the optical characteristics of the subject eye objectively measured by the measurement optical system 100 from the memory 82, and sets the optical characteristics as the initial value of the optometry unit 50. For example, the control unit 80 controls the driving of the symmetry unit 50, and switches the optical members corresponding to the optical characteristics of the measurement optical system 100, so as to arrange the optical members in the examination window 53. For example, if the optometry unit 50 is controlled and the initial value is completely set, the examiner performs the subjective examination of the subject eye while changing a correction degree of the optometry unit 50 and changing the examination visual target.

In this application example, the examiner sets either the far distance examination mode or the near distance examination mode. For example, in a case of the far distance examination mode, the far distance examination is performed. In addition, for example, in a case of the near distance examination mode, the near distance examination is performed.

For example, in a case where the far distance examination is performed (refer to FIG. 3A), the control unit 80 switches on the display 11. For example, the target light flux is output from the display 11 held by the holding unit 21 to the flat mirror 12. The target light flux is reflected by the flat mirror 12 and the concave mirror 13 respectively, and is guided again to the subject eye E by way of the flat mirror 12. In addition, for example, in a case where the near distance examination is performed (refer to FIG. 3B), the display 11 moves together with the holding unit 21, and is located at a near distance (for example, a distance of 40 cm away) from the subject eye E. The target light flux is output from the display 11 to the flat mirror 12. The target light flux is reflected on the flat mirror 12, and is guided to the subject eye E.

For example, at the time of the subjective examination, the examiner operates the controller 81 so as to display the examination visual target on a screen of the display 11. The control unit 80 retrieves the corresponding examination visual target data from the memory 82 in response to the input signal from the controller 81, and controls the display of the display 11. The examination visual target displayed on the display 11 is presented to the subject eye E of the examinee through the examination window 53 in the optometry unit 50 and the presentation window 3. For example, the examiner asks the examinee the visibility of the examination visual targets while switching the examination visual targets. As an example, for example, in a case where the examinee's answer is correct, the examiner switches the visual target to one level higher visual acuity value. In addition, as an example, for example, in a case where the examinee's answer is incorrect, the examiner switches the visual target to one level lower visual acuity value. In addition, for example, the examiner performs the examination while switching the visual targets and changing the correction degree for the examination visual target displayed on the screen. In this way, the examiner can acquire the subjective eye refractive power (for example, the spherical power S, the astigmatic power C, and the astigmatic axis angle A) of the subject eye at the set examination distance. As a matter of course, the optical characteristics of the subject eye other than the subjective eye refractive power may be acquired by performing the other subjective examination different from the above subjective examination.

For example, if the subjective examination is completely performed, the examiner performs an examination using a trial frame on the subject eye. For example, the examiner operates an upper switch 8a of the first operation unit 8 so as to raise the optometry unit 50 to the retracted position illustrated in FIGS. 1A and B. For example, if the upper switch 8a of the first operation unit 8 is operated, the control unit 80 drives a motor (not illustrated). For example, in a case where the optometry unit 50 is moved to the retracted position, the control unit 80 rotates a motor (not illustrated) in the rotation direction opposite to the rotation direction of the motor (not illustrated) when the optometry unit 50 is moved to the examination position.

For example, if the optometry unit 50 is completely moved to the retracted position, the examiner causes the examinee to wear the trial frame (trial frame or test frame), and checks the examinee's feeling of wearing while replacing the lenses (trial lenses) having different power (trial lens).

In this application example, the subjective optometry apparatus 1 may include the following configuration. While the subjective examination is performed, the objective measurement may be performed so as to recognize a change in the optical characteristics of the subject eye. For example, in this application example, while the subjective measurement is performed, adjustment information is acquired, based on the optical characteristics of the subject eye measured by the measurement optical system 100. For example, the adjustment information can be used in order to recognize the change in the optical characteristics of the subject eye while the subjective measurement is performed.

At the time of the objective measurement, the measurement results may be acquired in view of the optical members located in the optometry unit 50. For example, in a case where the optical members are located in the examination window of the optometry unit 50, the reflected light received through the optical member of the optometry window 53 is affected by the optical member. For example, the control unit 80 acquires the correction degree (change amount of the optical characteristics of the target light flux) of the optical member located in the optometry unit when the objective measurement is performed. For example, based on the correction degree, the control unit 80 corrects the measurement result obtained by objectively measuring the subject eye. In this manner, it is possible to correct the deviation of the optical characteristics which may be caused by a fact that the measurement light for measuring the objective measurement is guided by way of the optical member of the optometry unit 50.

More specifically, for example, in a case where the spherical power according to the correction degree of the optometry unit 50 is −1.0 D and the spherical power according to the optical characteristics measured by the objective measurement is −4.0 D, a difference between the spherical powers is acquired, thereby allowing the spherical power according to the optical characteristics measured by the objective measurement to be acquired as −3.0 D. In the above-described configuration, as the optical characteristics, the spherical power has been described as an example. However, this application example is not limited thereto. For example, as the optical characteristics, at least one of the spherical power, the astigmatic power, and the astigmatic axis angle may be used.

In a case where the above-described correction is performed, a light reception result (for example, a ring image) obtained by the detector may be corrected, or an objective value acquired from the light reception result may be corrected. That is, a configuration may be adopted so that the optical characteristics of the subject eye which are acquired by the objective measurement are corrected based on the correction degree (change amount of the optical characteristics of the target light flux).

1: subjective optometry apparatus
2: housing
3: presentation window
4: holding unit
8: first operation unit
9: second operation unit
10: projection optical system
11: display
40: observation unit
50: optometry unit
53: examination window
60: corneal position aligning optical system
80: control unit
82: nonvolatile memory 100: measurement optical system
105: light projecting optical system
110: objective optical system
120: light receiving optical system
121: detector
130: measurement light source
140: light receiving objective optical system
150: beam splitter

What is claimed is:

1. An optometry apparatus for measuring optical characteristics of a subject eye, comprising:
an optometry unit configured to have an optical member located in front of the subject eye and to change optical characteristics of a target light flux with the optical member, the optometry unit comprising an optical member comprising a lens for a left eye of the subject and an optical member comprising a lens for a right eye of the subject; and
a measurement optical system that includes a light projecting optical system having a measurement light source which emits measurement light and applying the measurement light emitted from the measurement light source to a fundus of the subject eye through the optometry unit, and a light receiving optical system in which a detector receives reflected light of the measurement light reflected on the fundus of the subject eye through the optometry unit, and objectively measures the optical characteristics of the subject eye,
wherein an optical axis of the measurement optical system is set to be off-axis from an optical axis of the optical member in the optometry unit, and
the optometry apparatus projects the target light flux on the subject eye through the optometry unit to subjectively measure the optical characteristics of the subject eye;
the optometry apparatus further comprising:
a projection optical system that has a visual target presenting portion configured to emit the target light flux, and that projects the target light flux emitted from the visual target presenting portion toward the subject eye; and
a housing that accommodates the projection optical system,
wherein the optometry unit is located outside the housing, and changes the optical characteristics of the target light flux emitted from the visual target presenting portion with using the optical member;
wherein the optical axis of the measurement optical system is inclined from the optical axis of the optical member in the optometry unit by an inclination angle from 1° to 25° or the optical axis of the measurement optical system is eccentric from the optical axis of the optometry unit by 0.5 mm to 15 mm.

2. The optometry apparatus according to claim 1,
wherein at least any one of an optical axis of the light projecting optical system and an optical axis of the light receiving optical system in the measurement optical system is set to be off-axis from the optical axis of the optical member in the optometry unit in order that the optical axis of the measurement optical system is set to be off-axis from the optical axis of the optical member in the optometry unit.

3. The optometry apparatus according to claim 2,
wherein an optical axis of the measurement light source in the light projecting optical system is set to be off-axis from the optical axis of the optical member in the optometry unit in order that the optical axis of the light projecting optical system is set to be off-axis from the optical axis of the optical member in the optometry unit.

4. The optometry apparatus according to claim 2,
wherein the light projecting optical system has an objective optical system applying the measurement light emitted from the measurement light source to the fundus of the subject eye through the optometry unit, and applies the measurement light to the fundus of the subject eye through the optometry unit, and
an optical axis of the objective optical system in the light projecting optical system is set to be off-axis from the optical axis of the optical member in the optometry unit in order that the optical axis of the light projecting optical system is set to be off-axis from the optical axis of the optical member in the optometry unit.

5. The optometry apparatus according to claim 1,
wherein the optical axis of the optical member in the optometry unit is coaxial with a visual axis that is set for the subject eye to view the target light flux projected on the subject eye in a frontal direction, and
the measurement optical system is located in order that the optical axis of the measurement optical system is off-axis from the optical axis of the optical member in the optometry unit.

6. The optometry apparatus according to claim 1,
wherein the light projecting optical system is located between the optometry unit and the housing.

7. The optometry apparatus according to claim 1,
wherein the light projecting optical system is located inside the housing.

8. The optometry apparatus according to claim 1, further comprising:
a holding unit configured to hold the optometry unit,
wherein the holding unit integrally links the housing and the optometry unit with each other.

9. The optometry apparatus according to claim 1, further comprising:
a correction unit configured to correct the optical characteristics of the subject eye measured by the measurement optical system, based on a change amount of the optical characteristics of the target light flux which is changed by the optical member.

10. The optometry apparatus according to claim 1, wherein the optical axis of the light projecting optical system is inclined from the optical axis of the optical member in the optometry unit by an inclination angle from 1° to 25°.

11. The optometry apparatus according to claim 1, wherein the optical axis of the light projecting optical system is inclined from the optical axis of the optical member in the optometry unit by an inclination angle from 5° to 20°.

12. The optometry apparatus according to claim 1, wherein the optical axis of the light projecting optical system is eccentric from the optical axis of the optometry unit by 0.5 mm to 15 mm.

13. The optometry apparatus according to claim 1, wherein the optical axis of the light projecting optical system is eccentric from the optical axis of the optometry unit by 1 mm to 10 mm.

* * * * *